(12) United States Patent
Hooykaas et al.

(10) Patent No.: US 7,314,737 B2
(45) Date of Patent: Jan. 1, 2008

(54) METHOD OF EFFECTING A CHANGE IN A CELL, AND A VECTOR

(75) Inventors: Paul Jan J. Hooykaas, Oegstgeest (NL); Annette Carolin Vergunst, Bussum (NL); Barbara Schrammeijer, Brookline, MA (US)

(73) Assignees: Stichting voor de technische Watenschappen in Utrecht (NL); Universiteit Leiden in Leiden (NL); Stichting Binair Vector Systeem in Oegstgeest (NL)

( * ) Notice: Subject to any disclaimer, the term of this patent is extended or adjusted under 35 U.S.C. 154(b) by 0 days.

(21) Appl. No.: 10/300,666

(22) Filed: Nov. 19, 2002

(65) Prior Publication Data

US 2004/0014025 A1   Jan. 22, 2004

Related U.S. Application Data

(63) Continuation-in-part of application No. PCT/NL01/00388, filed on May 21, 2001.

(30) Foreign Application Priority Data

May 19, 2000   (NL) .................................... 1015252

(51) Int. Cl.
  *C12P 21/04*   (2006.01)
  *C12N 15/00*   (2006.01)
(52) U.S. Cl. ..................... 435/71.1; 435/320.1
(58) Field of Classification Search ................ 435/453, 435/440, 449, 320.1
  See application file for complete search history.

(56) References Cited

U.S. PATENT DOCUMENTS 6,686,515 B1 * 2/2004 Lassner et al. ............. 800/294

FOREIGN PATENT DOCUMENTS

WO   WO 01/89283 A1   11/2001

OTHER PUBLICATIONS

Regensburg-Tuink et al. (Nature, vol. 363, pp. 69-71 (1993)).*
Hooykaas et al. (Ann. Rev. Phytopathol. 32:157-179 (1994)).*
Vergunst et al., Science 290:979-982, 2000.*
Folding@home Educational Project, website, 2005.*
International Search Report, International Application No. PCT/NL01/00388, dated Sep. 20, 2001 (3 pages).
Bravo-Angel, Ana Maria, et al., Bacterial Conjugation Protein MobA Mediates Integration of Complex DNA Structures into Plant Cells, 181(18) Journal of Bacteriology 5758-65 (Sep. 1999).
Bundock, Paul, et al., "Trans-kingdom T-DNA transfer from *Agrobacterium tumefaciens* to *Saccharomyces cerevisiae*," 14(13) The EMBO Journal 3206-14 (1995).
Citovsky, Vitaly, et al., "Nuclear Localization of Agrobacterium VirE2 Protein in Plant Cells," 256 Science 1802-5 (Jun. 26, 1992).
Howard, Elizabeth A., et al., "The VirD2 Protein of *A. tumefaciens* Contains a C-Terminal Bipartite Nuclear Localization Signal: Implications for Nuclear Uptake of DNA in Plant Cells," 68 Cell 109-18 (Jan. 10, 1992).
Shurvinton, Claire E., et al., "A nuclear localization signal and the C-terminal omega sequence in the *Agrobacterium tumefaciens* VirD2 endonuclease are important for tumor formation," 89 Proc. Natl. Acad. Sci. USA (11837-41 (Dec. 1992).
Vergunst, Annette C., et al., "Cre/lox-mediated site-specific integration of Agrobacterium T-DNA in *Arabidopsis thaliana* by transcient expression of cre," 38 Plant Molecular Biology 393-406 (1998).
Vergunst, Annette C., et al., "VirB/D4-Dependent Protein Translocation from Agrobacterium into Plant Cells," 290 Science 979-82 (Nov. 3, 2000).
Zhou, Xue-Rong, et al, "Mutagenesis of the Agrobacterium VirE2 Single-Stranded DNA-Binding Protein Identifies Regions Required for Self-Association and Interaction with VirE1 and a Permissive Site for Hybrid Protein Construction," 181(14) Journal of Bacteriology 4342-52 (Jul. 1999).

* cited by examiner

*Primary Examiner*—Nancy Vogel
(74) *Attorney, Agent, or Firm*—TraskBritt

(57) ABSTRACT

A method of effecting a change in a cell using a transfer system which is contacted with the cell to be changed. The transfer system comprises a fusion protein which is transferred into the cell using the VirB/VirD4 transfer system. According to the invention, a fusion protein BA is introduced into the cell to be changed comprising i) as a first part A, an oligopeptide comprising the C-terminal amino acids 1-20 of VirF, VirD2, VirE2, VirE3, VirD5 or MobA, or an analogue thereof and ii) as a second part B, a polypeptide capable of effecting a cell-changing activity in the cell to be changed, wherein the polypeptide is attached with the C-terminal end thereof linked with the N-terminal end of the first part.

16 Claims, 5 Drawing Sheets

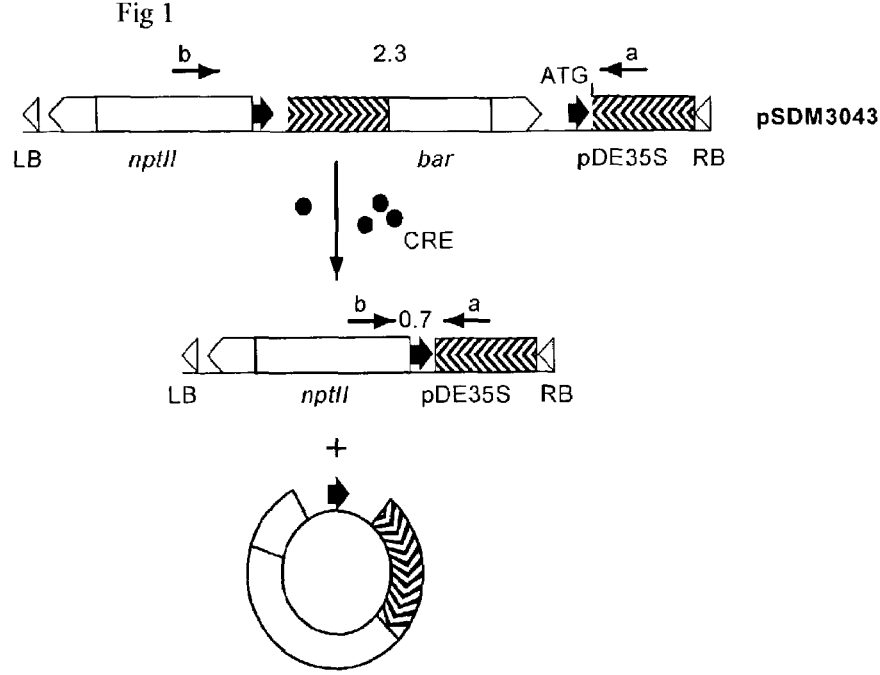
FIG. 2.
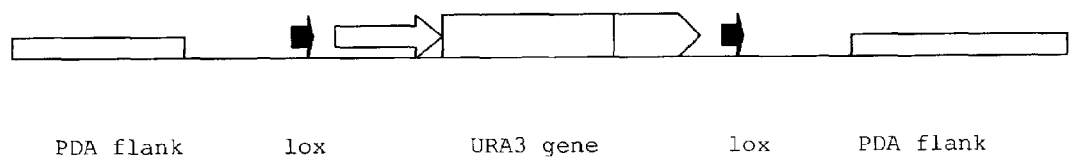

METHOD OF EFFECTING A CHANGE IN A CELL, AND A VECTOR

CROSS-REFERENCE TO RELATED APPLICATIONS

This application is a continuation-in-part application of PCT International Application No. PCT/NL01/00388, filed on May 21, 2001 and designating the United States of America, published in English on Nov. 21, 2001 as WO 01/89283 A1, the contents of the entirety of which are incorporated herein by this reference.

TECHNICAL FIELD

The invention relates generally to biotechnology and, more specifically, to a method of effecting a change in a cell, wherein a transfer system is contacted with the cell to be changed, the transfer system comprising a membrane including a protein transport system comprising a pore which comprises a VirB complex and VirD4 protein, wherein the transfer system comprises a fusion protein or is capable of making a fusion protein which is introduced into the cell by means of the protein transport system.

BACKGROUND

Zhou, X-R et al. (Journal of Bacteriology, 181 (14), p. 4342-4352 (1999)) discloses that the protein VirE2, a single-stranded DNA-binding protein of *Agrobacterium tumefaciens*, can be transferred into a host cell by a tumorigenic *Agrobacterium*. Zhou et al. disclosed that they were only at amino acid 39 (from the N-terminus, as is customary in the art) able to introduce a heterologous amino acid sequence which was transferred to the host cell. Zhou et al. concluded that it was not practically feasible to base a protein delivery system on fusions at one of the two ends of VirE2. Small proteins at least are tolerated as an insertion at amino acid 39.

DISCLOSURE OF THE INVENTION

The invention provides a method of effecting a change in a cell, wherein a transfer system is contacted with the cell to be changed, the transfer system comprising a membrane including a protein transport system comprising a pore which comprises a VirB complex and VirD4 protein, wherein the transfer system comprises a fusion protein or is capable of making a fusion protein which is introduced into the cell by means of the protein transport system, which method is simple to perform and, if desired, is performed without native activity of VirE2 in the cell to be changed.

Accordingly, a method according to the invention is characterized in that a fusion protein BA is introduced into the cell to be changed in which fusion protein BA:

i) comprises, as a first part A, an oligopeptide comprising the C-terminal amino acids 1-20 of VirF, VirD2, VirE2, VirE3, VirD5 or MobA, or an analogue thereof and ii) comprises, as a second part B, a polypeptide capable of exercising a cell-changing activity in the cell to be changed, wherein the C-terminal end of the polypeptide is linked to the N-terminal end of the first part A, under the condition that if the fusion protein comprises a first part A derived from VirE2, the fusion protein does not comprise the 84 N-terminal amino acids of VirE2.

Surprisingly, it has been found that, provided the above-mentioned conditions are met, a protein can be introduced from the outside into a cell to be changed, which protein is formed by coupling the polypeptide (second part B) to an (internal) N-terminal amino acid of VirF, VirD2, VirE2, VirE3, VirD5 or MobA or an analogue thereof (first part A), as a result of which the activity of the introduced second part B may be expressed in the cell to be changed, as a result of which the cell is changed. This change may be temporary (reversible) or permanent (irreversible). The amino acid sequences of VirF, VirD2, VirE2, VirE3, VirD5 and MobA are represented by the respective sequence nos. 1-6. A strain comprising a plasmid (LBA8250, a *Agrobacterium tumefaciens* strain, containing plasmid pTi15955. pTi15955 is described by Sciaky et al., Plasmid 1, p. 238-253 (1978)) coding for all vir proteins, is in the Phabagen collection of the Centraalbureau voor Schimmelcultures (CBS), Baarn, the Netherlands, under accession number PC2692. MobA protein is known from incQ plasmid RSF1010, as present in *E. coli* strain K12 C600 with accession number PC-V3110 of the NCCB collection of the CBS, and described by Scholz, P. et al. in Gene 75, p. 271-288 (1989).

As is shown in the Examples, the C-terminal parts of the peptides as mentioned can be shortened from the N-terminal end without significant loss of functionality of transport. Evidence is provided that the minimum number of amino acids of the C-terminal part of VirF required for the functionality of transport is about 20 amino acids, where a number of about 40 amino acids seems to be optimal. Further, a sequence comparison (with hand alignment, see Table 2) of the C-terminal parts of the sequences 1-6 has determined that all the sequences show the presence of at least two arginine(R) residues in the last few amino acids, while some have even four or more R residues in the C-terminal 20-mer. Also it is apparent from the sequences as presented that this C-terminal 20-mer predominantly consists of hydrophilic and neutral amino acids. Generally, no more than 10% of the amino acids are hydrophobic, but preferentially no more than 20%, more preferentially no more than 30%, even more preferentially not more than 40% and most preferably not more than 50%. It is to be understood that analogues of the C-terminal peptides as disclosed in this invention can also be used. Analogues can be formed by replacing, adding or deleting one or more amino acids from the C-terminal peptides of the amino acid sequences of virF, virE2, virE3, virD2, virD5 and mobA, but they still should comply with the above requirements (the C-terminal 20-mers having at least two R (or K, see below) residues and predominantly consisting of hydrophilic and neutral amino acids). For replacing amino acids, preferably corresponding amino acids are taken, but it is also envisaged that the amount of arginines/lysines and/or the amount of hydrophilic amino acids is increased. For example, it is very well possible to replace one or more of the R residues with a lysine (K) residue, without severe loss of functionality of transport.

In the present invention, a corresponding amino acid is an amino acid according to the following table:

A, G;
S, T;
D, E;
N, Q;
R, K;
I, L, M, V; and
F, Y, W.

The first part A may, if desired, comprise more amino acids from amino acid 21 (as from the C-terminus) of VirF, VirE2, VirE3, VirD2, VirD5 or MobA with the proviso for VirE2 as previously mentioned. Most preferred is a C-terminal part consisting of 40 amino acids of the mentioned peptides.

In the present invention, a vector is understood to be any DNA or RNA sequence which, directly or indirectly, leads to the formation of the fusion protein in the transfer system. Such a vector may be derived from an *Agrobacterium* Ti or Ri plasmid, but can also be derived from plasmids generally used in the area of transformation such as broad host range plasmids (e.g., pBBR, pBR322, pUC14, pBLUEscript, pGREEN and the like). Useful plasmids can also be found in the experimental section.

The vector will include all elements necessary for the production of the fusion protein AB as defined above and/or the protein transport proteins VirB and VirD4, such as promoters, transcriptional and translational enhancers, and terminators.

The transfer system may be a cell, such as, very suitably, a bacterial cell, such as in particular *Agrobacterium tumefaciens*, but may also be an artificial system, such as a minicell or an artificial vesicle system. It is to be understood that the transfer system further comprises all necessary elements to enable functionality of the system. In the case of *Agrobacterium*, this means that all the (genetic) information for survival or fitness of the bacterium needs to be present.

The fusion protein to be transferred can either be formed in the transfer system itself, for example, by expressing a vector containing a functional gene system that may be expressed yielding the fusion protein, or the fusion protein itself may be introduced into the transport system. In artificial transport systems, generally the latter will be the case. An important advantage of such an artificial transport system is that it may be introduced into the environment, for example, for treating a crop, without risk of spreading genetic material.

BRIEF DESCRIPTION OF THE FIGURES

FIG. 1 Schematic drawing of the test system in plants.

FIG. 2 Schematic drawing of the test system in yeast.

DETAILED DESCRIPTION OF THE PREFERRED EMBODIMENTS

Figure 3:
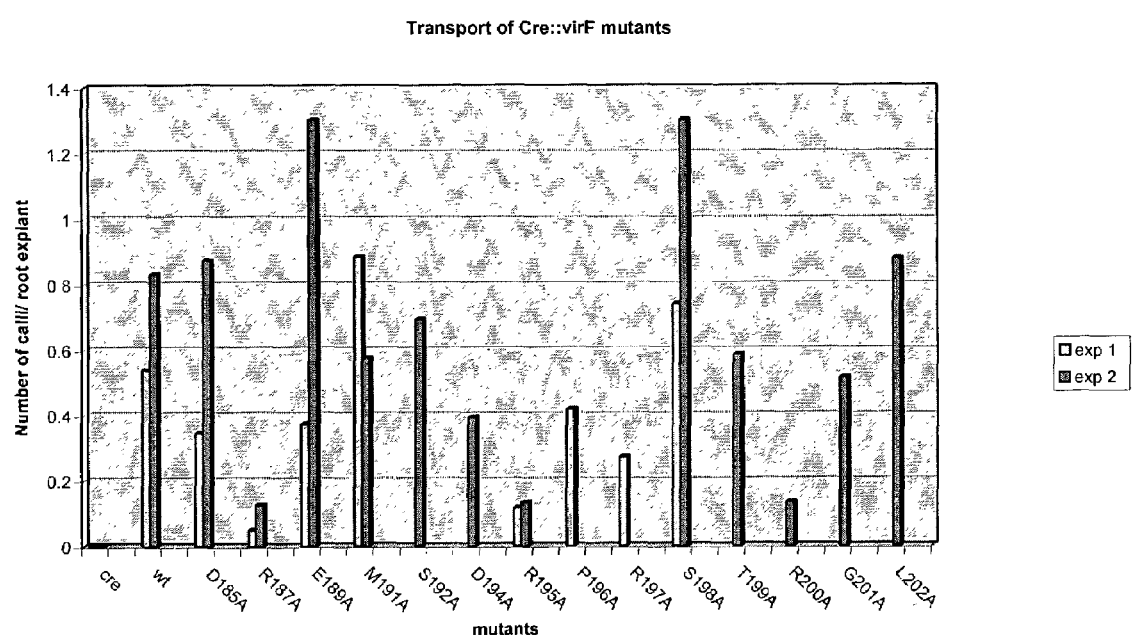
FIG. 3 Analysis of transport of Cre::virF fusion proteins into *Arabidopsis* excision line 3043 in two independent experiments. Cre: LBA1100 containing pSDM3147, wt: LBA1100 constaining pSDM3155 (Cre::virFdel1-126 wt), D185A, R187A, E189A, M191A, S192A (only exp. 2), D194A (only exp. 2), R195A, P196A (only exp. 1), R197A (only exp. 1), S198A, T199A (only exp. 2), R200A (only exp. 2), G201A (only exp. 2), L202A (only exp. 2): Single point mutations in cre::virFdel1-126.

Preferably, the fusion protein is introduced into the cell without the introduction of a DNA or RNA sequence. In case of the use of *A. tumefaciens* as the transfer system, this implies the absence of T-DNA. This means that it is possible to change a cell without introducing genetic material into the cell to be changed.

According to one embodiment, the fusion protein introduced has recombinase activity. In such a case, it is, in fact, possible to effect a change in the chromosomal DNA of the cell to be changed without introducing additional genetic material (a vector coding for the T-DNA or peptide B) into the cell. An important application is, for example, the removal of a marker gene, whose admittance in the environment is undesirable. In particular, this may include the removal of antibiotic-resistance genes present between DNA sequences in direct repeat to be recognized by the recombinase.

Conveniently, a bacterium of the class of Rhizobiaceae may be used as a transfer system, such bacteria amongst which *Agrobacterium, Rhizobium* and *Phyllobacterium* are very suitable for modification of plants, yeasts or fungi. Other bacteria belonging to this family, such as *Brucella*, are known for their interaction with human and animal cells and may be used for modification thereof. Especially *Brucella* or other bacteria which can interact with mammalian cells are of particular interest for changing these cells. In this way, it would be possible to administer (proteinaceous) drugs which would not survive conventional dosage regimens, e.g., due to the presence of proteases. Also, vaccines based on such a protein delivery are envisaged.

According to a preferred embodiment, use is made of *Agrobacterium*, which is known to be very suitable for the modification of both prokaryotes (bacteria), and eukaryotes (plants, yeasts, fungi, and animal cells).

According to a preferred embodiment, a cell chosen from the group consisting of i) a plant cell; ii) a yeast cell; and iii) a fungal cell, is used as the cell to be modified. Such a cell may be changed according to the present invention in vitro or in vivo. When cells are changed in vitro, it is further envisaged that these cells can be used for regeneration of the organism (such as regeneration of plants or fungi and yeasts), but also, in the case of animal cells, for re-introduction into the body. This latter embodiment would be useful for overcoming (epi)genetic defects in mammalians, for example, by inducing directed (epi)genetic changes in pancreatic cells that do not correctly express insulin in diabetics.

The invention also relates to a vector, the vector being characterized in that it codes for a protein transport system comprising a pore which contains a VirB complex and VirD4 protein, as well as for a fusion protein BA that comprises i) as a first part A an oligopeptide comprising the C-terminal amino acids 1-20 of VirF, VirD2, VirE2, VirE3, VirD5 or MobA, or a part or an analogue thereof, and ii) as a second part B a polypeptide capable of effecting a cell-changing activity in the cell to be changed, wherein the polypeptide with its C-terminal end is linked to the N-terminal end of the first part A, under the condition that if the fusion protein comprises a first part A derived from VirE2, the fusion protein does not comprise the 84 N-terminal amino acids of VirE2. As stated above, also vectors which only code for a protein transport system comprising a pore which contains a VirB complex and VirD4 protein are part of the embodiment of the invention in which the fusion protein is added to the cell containing the vector.

Such a vector may be introduced into a transfer system, such as a bacterium. A vector according to the invention will possess the minimal information that needs to be expressed for the transfer of the fusion protein, making it possible for the fusion protein to be transferred to the cell to be changed.

Finally, the invention relates to a vector set, which is characterized in that the vector set comprises one or more vectors coding for a protein transport system comprising a pore which contains a VirB complex and VirD4 protein as well as a further vector coding for a fusion peptide BA which comprises i) as a first part A an oligopeptide comprising the C-terminal amino acids 1-20 of VirF, VirD2, VirE2, VirE3, VirD5 or MobA, or a part or an analogue thereof, and ii) as a second part B a polypeptide capable of exercising a cell-modifying activity in the cell to be modified, wherein the polypeptide of the C-terminal end of the polypeptide is linked to the N-terminal end of the first part A, under the condition that if the fusion protein comprises a first part A derived from VirE2, the fusion protein does not comprise the 84 N-terminal amino acids of VirE2.

The advantage of such a vector set is that the vector or vectors coding for the protein transport system may be introduced into a transfer system separate from further vector coding for the fusion protein. This makes it possible to use a transfer system, in particular a bacterium, as a standard vehicle for modifying a cell, wherein the transport system is provided with a further vector which is expressed in the transport system for effectuating the modification.

The protein translocation system of the invention can be used, amongst others:

a) for induction of systemic resistance to pests and diseases in plants, for example, by spraying plants with bacteria that transfer an anti-pathogenic protein, such as a chitinase, glucanase or osmotin, or with bacteria that contain a protein which triggers a so-called hypersensitive response, such as an avr protein or a mutated ndr protein;

b) for transdermal, subcutaneous, oral, intranasal, gastrointestinal or pulmonary delivery of a proteinaceous drug. This is especially useful for proteinaceous drugs, which application is hampered by their sensitivity to degradation in the body, e.g., by protease activity on the skin or in the mucosa. Also, it is deemed to be particularly useful to improve existing or design novel drugs that will provide solutions for unmet medical needs such as colon and skin cancer (antineoplastics), diabetes, psoriasis, infections (anti-inflammatory drugs) and genetic defects;

c) for development of vaccines for both human and veterinary applications;

d) for development of in vivo or in vitro diagnostic products, for instance, by introducing an enzyme that is capable of detecting a specific metabolite in plant, fungal (including yeast) or animal cells by converting it into a (fluorescent) dye or by enhancing the expression of a gene in the acceptor cell, which gene product can easily be detected;

e) for drug development. For this it is envisaged that a (high throughput) screen can be developed in 96-well or 384-well plates for peptides or proteins that result in a desirable and scorable effect in plant, fungal (including yeast) and animal cells, using, for instance, a (reverse) two-hybrid approach in yeast (Vidal and Endoch, TIBTECH, 17, 374-381, 1999) to screen for peptides that disrupt or allow a protein-protein interaction and thereby prevent or allow expression of a reporter gene, which expression can be detected by survival of the cells (FAO selection) or by a fluorescent dye (GFP, alkaline phosphatase).

The invention will be illustrated with reference to the following Examples and to the drawing in which FIGS. 1 and 2 schematically show a test system to demonstrate Cre activity in planta (FIG. 1) and in yeast (FIG. 2), respectively.

EXAMPLES

Bacterial Strains

*Agrobacterium* strain LBA1010 (Koekman et al., Plasmid 7 (1982); 119-132; Centraal Bureau voor Schimmelcultures; Baarn, the Netherlands, accession number: PC2805) possesses the wild type Ti-plasmid pTiB6 in a C58 chromosomal background. LBA 1100 (Beijersbergen et al., Science 256 (1992), 1324-1327; easily obtained by culturing CBS 102794, Centraal Bureau voor Schimmelcultures; Baarn, the Netherlands, deposited on 17 May 2000 in the absence of gentamycin for curing of plasmid pSDM 3155 and screening for the absence of the small (ca. 5.5 kb) plasmid) is a non-oncogenic derivative of LBA1010. To this end, both the left and right T regions in pTiB6 as well as tra and occ genes are replaced by a spectinomycin-resistance marker, resulting in plasmid pAL1100, wherein the Vir region remained intact. For the present application, several vir mutants, derived from LBA1100, resp. LBA 1142-1150 (Beijersbergen et al., Science 256 (1992), 1324-1327) were used (Table 1). LBA2561 contains a precise deletion of the virF gene in pAL1100 (Schrammeijer et al., Mol. Plant. Micr. Int. 5 (1998), 429-433). Transformation and growth of bacterial strains were performed as described elsewhere (Vergunst et al., Nucl. Acids Res. 26 (1998) 2729-2734) or according to general techniques known to the person skilled in the art (Sambrook et al., Molecular cloning. A lab manual. (1989)).

Plasmid Constructions

The coding region of the cre gene was cloned translationally to the virE2 and virF gene of pTi15955, under control of the respective vir promoter regions. Both N-terminal and C-terminal fusions were made. The plasmid constructions are detailed below.

The cre Control Plasmid

The coding region of the cre recombinase gene, present in plasmid pUC19cre (Mozo & Hooykaas, Mol. Gen. Genet. 236 (1992), 1-7), was cloned as an SphI/EcoRI fragment into pUC21 (Vieira & Messing, Gene 100 (1991), 189-194), resulting in pSDM3120. In order to remove the ATG starting codon, a PCR amplification was performed at the 5'-end of the cre gene with the primers cre1 (5'-ggc agatctgTCCAATTTACTG) (SEQ ID NO:1) and cre2 (5'-GATAATCGCGAACATCTTCAGG) (SEQ ID NO:2) on pSDM3120. After digestion of the PCR fragment with BglII and NruI (underlined), this fragment was exchanged for the corresponding fragment in pSDM3120 (resulting in creΔATG or pSDM3121). An SalI fragment of pRAL3248 (Melchers et al., Plant Mol. Biol. 14 (1990), 249-259) into which virE1 and virE2 (the last 30 3'-terminal base pairs being absent) including the virE promoter region are located, was cloned into the XhoI restriction side of pSDM3121 (pSDM3122). After full digestion of pSDM3122 with BglII and partial digestion with BstYI, followed by isolation of the vector fragment carrying the virE promoter, the virE1 coding area, the ATG starting codon of virE2, as well as cre (ΔATG), the cre gene was translationally linked through self closure to the ATG starting codon of virE2 (pSDM3126). As a result, the expression of the cre gene is controlled by the virE promoter. Subsequently, this construct was transferred as an StuI/XbaI fragment to the SmaI/XbaI-digested plasmid pRL662, resulting in pSDM3147, i.e., the cre control plasmid used in these experiments. The non-mobilizable plasmid pRL662 with a broad host range is obtained by replacing the kanamycin resistance gene as well as the mob region of pBBR1MCS2 (Kovach et al., BioTechn. 16 (1994), 800-802) with a gentamycin resistance marker (J. Escudero, European patent application 00200726.8).

The cre::virE2 Fusion

In order to create translational fusions between cre and virE2, the STOP codon of the cre gene was removed; to this end, a mutation in the STOP codon (italics) was introduced using PCR amplification on pSDM3126 DNA using the primers cre 6 (5'-acgc gtcgactATCGCCATCTTCCAGCAGGCGC) (SEQ ID NO:3) and cre 7 (5'-cC ATCGATTGATTTACGGCGCTAAGG) (SEQ ID NO:4). After digestion with ClaI and SalI (underlined), the corresponding ClaI-SalI fragment of pSDM3126 was replaced (resulting in creΔSTOP or pSDM3127). An XhoI/NotI fragment of pBluevirE2 (ΔATG) containing the virE2 coding area, without the ATG start codon, was subsequently ligated into the vector pSDM3127 digested with SalI and NotI (pSDM3128). pBluevirE2 (ΔATG) was the result of cloning the VirE1-virE2 region (XhoI-SmaI) of plasmid pRAL3248 (Melchers et al., Plant Mol. Biol. 14 (1990), 249-259) in pBLUEscript (XhoI/EcoRV) (Alting-Mees and Short, Nucleic Acids Res. 17 (1989): 9494), subsequent to which virE1 and the ATG start codon of virE2 were removed using an XhoI-StuI linker (5'-tcgaGATCTTTCTGGCAAT-GAGAAATCCAGG (SEQ ID NO:5) and 5'-CCTG-GATTTCTCATTGCCAGAAAGATC (SEQ ID NO:6). The cre::virE2 fusion was subsequently transferred to pRL662 (SmaI/XbaI) as an StuI/XbaI fragment of pSDM3128, resulting in pSDM3129 (cre::virE2 fusion).

The virE2::cre Fusion

An SalI fragment of pRAL3248 comprising virE1 and virE2 (the last 30 3'-terminal bases being absent) was cloned into pIC19R (Marsh et al., Gene 32 (1984): 481-485) (pSDM3123). In the subsequent cloning steps, cre was fused to the 3'-end of virE2, wherein at the same time, the last 30 3'-terminal bases of virE2, absent in pSDM3123, were restored. To this end, a BglII/NruI fragment of pSDM3122, comprising the 200 5'-terminal bases of cre, without the ATG start codon, was cloned into pIC19R (pSDM 3151). An SalI/BglII linker, consisting of the last 30 3'-terminal bases of virE2, was synthesized in order to remove the STOP codon of virE2 (italics) (5'-TCGACCGCGTAGCCAAAGCGTCAACAGCTTTcga (SEQ ID NO:7) and 5'-gatctcgAAAGCTGTTGACGCTTTGGCTACGCGG (SEQ ID NO:8)) and to effect translational fusion with cre. This linker was cloned into pSDM 3151 (pSDM3152). However, after sequence analysis, the BglII site between the 3'-end of virE2ΔSTOP and the 5'-end of creΔATG was shown to be lost due to a single base substitution. This mutation is not present in the region coding for virE2 or cre, and has no effect on the reading frame of the fusion. The SalI fragment of pSDM3123 was introduced into the SalI site of pSDM3152 (pSDM3157), cloning the complete virE2 sequence in frame with the 5'-end of cre. An NruI fragment of about 600 base pairs from pSDM3157 (the 3'-end of virE2ΔSTOP and the 5'-end of creΔATG) was subsequently used to replace the NruI fragment in pSDM3148 (pSDM3148 is the result of cloning an StuI/XbaI fragment of pSDM3122 into pRL662 XbaI/SmaI, resulting in a translational fusion between the complete virE2 region and cre (pSDM3166, i.e., the virE2::cre fusion) under control of the virE promoter and joint expression of VirE1.

The virF::cre Fusion

A 600 base pair SacI/EcoRV fragment of pRAL7088 (Schrammeijer et al., MPMI 11 (1998) 429-433) containing the 5' flanking side of virF and the ribosomal binding place was cloned into pBluescriptSK⁻ (Alting-Mees and Short, Nucleic Acids Res. 17 (1989): 9494), resulting in pSDM3183. The nuclear localization signal (NLS) of simian virus 40 (SV40) was synthesized with an EcoRV blunt and a 3' SalI sticky end (5'-ATCATGGATAAAGCGGAAT-TAATTCCCGAGCCTCCAAAAAAGAA-GAGAAAGGTCG AATTGGGTACCGG (SEQ ID NO:9) and the complementary strand) and cloned into pSDM3183, resulting in pSDM3184. The virF gene without the ATG and STOP codon was cloned in two steps in frame after SV40 NLS. The ATG start codon was removed by cloning a BamHI/NsiI linker (5'-GATCCGAAATTCGAGTTTGCGT-GATGCA) (SEQ ID NO:10) in the BamHI and NsiI sites of pRAL7088 (pSDM3192). Subsequently, a BamHI/SacI fragment of 1.5 kilobase pairs of pSDM3192 was cloned into pIC19H (pSDM3193). An SalI/XhoI fragment of 500 base pairs of pSDM3193 comprising virFΔ498-609ΔATG was cloned in frame with the SV40 NLS into the XhoI site of pSDM3184, resulting in pSDM3185. Subsequently, the STOP codon of virF was removed using two primers (5'-ATCCCTAACTTGGTCTTCAAC (SEQ ID NO:11) and 5'-cttagatcTAGACCGCGCGTTGATCGAGG) (SEQ ID NO:12) in a PCR reaction on pRAL7088. The PCR fragment was subcloned as a 175 bp fragment into vector pGEM T (Promega). A 16 base pair StuI/BglII linker (5'-c ctcgagcccgggata (SEQ ID NO: 13) and 5'-gatctatcccgg gctcgagg (SEQ ID NO:14)) was cloned into pSDM3121 digested with StuI/BglII to introduce an XhoI site (underlined) and to effect further in-frame cloning of cre with virF (pSDM3121-L). Subsequently, the 3'-end of virF was cloned in frame into the XhoI/BglII sites of pSDM3121-L as an XhoI/BglII fragment of about 110 base pairs from the pGEM-T vector to the 5'-end of cre (resulting in pSDM3186). A 1.2 kb XhoI/SalI fragment of pSDM3186 was ligated into the XhoI site of pSDM3185, resulting in pSDM3187. The virF::cre fusion was subsequently introduced into pUC28 (Benes et al., Gene 130 (1993); 151-152) as a SacI/PstI fragment and subsequently ligated from this plasmid as an EcoRI fragment into the EcoRI site of pRL662, resulting in pSDM3153, i.e., the NLS::virF::cre fusion plasmid.

The cre::virF Fusions

A 0.66 kb fragment of pSDM3184, having the 5' flanking side of virF and the SV40 NLS sequence, was eventually cloned via an SacI/SalI cloning step into pIC19H, followed by an HindIII/SalI cloning into pIC19R, as an SalI/XhoI fragment into the XhoI site of pSDM3121. This resulted in an in-frame fusion of the SV40 NLS to the 5'-end of cre (pSDM3188). The STOP codon of cre in pSDM3188 was subsequently removed by replacing the ClaI/SalI fragment (with the 3'-end of cre including STOP) with the ClaI/SalI creΔSTOP fragment of pSDM3127 (pSDM3179). A 690 bp SalI/EagI fragment of pSDM3193 comprising virFΔATG was cloned into pSDM3179 digested with SalI/NotI, resulting in pSDM3189. An HindIII/XbaI fragment of pSDM3189 was cloned into the HindIII and XbaI sites of pRL662, resulting in pSDM3154 (the NLS::cre::virF fusion plasmid).

In addition, a number of deletions was made of virF and cloned translationally to the 3'-terminus of cre. Using the primers F126 (5'-acgcgtcgaCCTGTCGAGTCGGCTGAG (SEQ ID NO:15), position 127 in virF) and pflF2 (5'-GACCAGCACACTTAGATACC (SEQ ID NO:16)) in the DNA sequence adjacent to 3' virF), a PCR reaction was performed on pRAL7088. The PCR fragment of 780 base pairs was cloned into vector pT7pBlue-T (Novagen) (pSDM3194). An SalI/EagI fragment (virFΔ1-126) of 555 base pairs of pSDM3194 was cloned into pSDM3179, resulting in pSDM3190. Cloning the NLS::cre::virFΔ1-126 fusion into vector pRL662 as an HindIII/XbaI fragment resulted in pSDM3155 (the NLS::cre::virFΔ1-126 fusion plasmid).

The 113 3'-terminal nucleotides of virF were cloned in frame with cre. To this end, pSDM3189 was transferred as an HindIII/XbaI fragment to pUC18 (Yanish-Perron et al., Gene 33 (1985), 103-119), resulting in pSDM 3172. Digestion of pSDM3172 with XhoI and SalI, removal of the 5'-sticky end using Mung bean nuclease followed by self-closure of the vector resulted in an in-frame fusion of the last 112 3'-terminal base pairs of virF with cre (pSDM3173). Transfer of the NLS::cre::virFΔ1-498 fusion to pRL662 as an XbaI/HindIII fragment resulted in plasmid pSDM3174 (the NLS::cre::virFΔ1-498 fusion plasmid).

The plasmids were transferred to the bacterial strains shown in Table 1. In addition, the plasmid pSDM3191, on which the genes virD3 and virD4 are located under the control of the virD promoter, was mobilized in LBA1147 and LBA1150. pSDM3191 is the result of cloning a 4.4 kilobase pair BamHI fragment of pMP3 (Vogel and Das, J. Bacteriology 174 (1992), 5161-5164) in the BamHI restriction site of pLM997 (Melchers, unpublished), which is the result of replacing the T-region of pBin 19 (Bevan et al., Nucleic Acids Res. 12(1984), 8711-8721) with a pIC19R/H polylinker sequence (Marsh et al., Gene 32 (1984), 481-485).

TABLE 1

| Strain | Plasmid | Resistance-markers |
|---|---|---|
| LBA1010 | pTiB6 | Rif |
| LBA1100 | pTiB6ΔT₁,T₁, Δtra, Δocc | Rif, Sp |
| LBA2561 | pAL1100ΔvirF | Rif, Sp |
| LBA1142 | pAL1100(virΔ::Tn3Hohol) | Rif, Sp, Cb |
| LBA1143 | pAL1100(virB4::Tn3Hohol) | Rif, Sp, Cb |
| LBA1144 | pAL1100(virB7::Tn3Hohol) | Rif, Sp, Cb |
| LBA1145 | pAL1100(virG::Tn3Hohol) | Rif, Sp, Cb |
| LBA1146 | pAL1100(virC2::Tn3Hohol) | Rif, Sp, Cb |
| LBA1147 | pAL1100(virD2::Tn3Hohol) | Rif, Sp, Cb |
| LBA1148 | pAL1100(virD4::Tn3Hohol) | Rif, Sp, Cb |
| LBA1149 | pAL1100(virE2::Tn3Hohol) | Rif, Sp, Cb |
| LBA1150 | pAL1100(virD1::Tn3Hohol) | Rif, Sp, Cb |

The NLS::cre::virF-fusion gene was also coupled to the helper plasmid in LBA2561 by selecting for single cross-overs between the homologous DNA regions flanking the virF gene and NLS::cre::virF (pSDM3189), resulting in LBA2561::NLS::cre::virF.

As a control for transformation of the plant, LBA1115 (=MOG101, (Hood et al., Transgenic Res. 2 (1993), 208-218) was used, which is comparable to LBA1100 but containing tra and occ genes. IncP-vector pSDM3088 (Vergunst & Hooykaas, Plant Mol. Biol. 38 (1998), 393-406), containing the cre gene under control of the mannopine synthase promoter between the left and right adjacent sequences of Agrobacterium ("T-DNA border repeats"), was transferred to LBA1115.

Plant Lines

Plasmid pSDM3043 (see FIG. 1 and Vergunst & Hooykaas, Plant Mol. Biol. 38 (1998), 393-406) was introduced into Arabidopsis thaliana C24 by means of the Agrobacterium-mediated transformation of root explants (Vergunst et al., in Methods in Mol. Biol. 82 pp 227-244 (1998)) and transformants were selected for resistance to phosphinothricin (30 mg/l). Plants having the excision locus 3043 are sensitive to kanamycin. A transformed plant, with 3:1 segregation for the transgene (1 locus), was selected based on the efficiency of the Cre-mediated excision of the bar gene (see FIG. 1), flanked by lox sites present in direct repeat (see arrows in the drawing). Cre-mediated excision could be accomplished by transforming root explants with the Cre-expression vector pSDM3088. Such an excision simultaneously resulted in repair of a kanamycin resistance-marker.

Plant Transformation

The protocol for transformation of Arabidopsis root explants mediated by Agrobacterium was described earlier (Vergunst et al., in Methods in Mol. Biol. 82 pp 227-244 (1998)). Roots of 10-day old seedlings being homozygous for the excision locus 3043 (T3 or T4) were used in transformation assays using the strains disclosed in Table 1 containing the constructs described above. After co-cultivation for 2 days, the explants were transferred to a medium for inducing the growth of calli and shoots, which medium contained 50 mg/l kanamycin and 100 mg/l Timentin. The number of kanamycin-resistant calli was determined 2 and 3 weeks after co-cultivation. PCR analysis was performed on a number of shoots regenerated from calli resistant to kanamycin.

Construction of a Saccharomyces cerevisiae Strain Containing a Floxed URA3 Gene The URA3 gene was cloned as an HindIII fragment from pJJ244 (Jones and Prakash (1990) Yeast, 6, 363-366) into the filled-in EcoRI site of pIC-2lox (Meijer et al. (1998) Yeast, 14, 1407-15) resulting in pSDM3011. The resulting floxed URA3 gene was subcloned as an HindIII fragment into pUC4α10 (Steensma et al. (1990) Eur. J. Biochem., 191, 769-74), which contains part of the PDA1 locus (pSDM3012). Finally, the PDA1-lox-URA3-lox-PDA1 cassette was cloned into binary vector pBin19 (Bevan (1984) Nucl. Acids Res., 12, 8711-21) resulting in pSDM3013. *A. tumefaciens* strain LBA1126 (Bundock and Hooykaas (1996) Proc. Natl. Acad. Sci. USA, 93, 15272-5) was electroporated (den Dulk-Ras and Hooykaas (1995) Methods Mol. Biol., 55, 63-72) with pSDM3013 and used in a co-cultivation experiment with *S. cerevisiae* strain RSY12 (MATa leu2-3, 112 his3-11, 15 ura3Δ::HIS3) (Schiestl and Petes (1991) Proc. Natl. Acad. Sci. USA, 88, 7585-9). Transformants, prototrophic for uracil, were selected on MY medium (Zonneveld (1986) J. Microbiol. Methods, 4, 287) containing 200 µM cefotaxime (Duchefa, B. V.), leucine (30 mg/l) and histidine (20 mg/l) but lacking uracil. Transformants were further characterized with polymerase chain reaction (PCR) and Southern blot analysis. Strain LBY2, in which the loxURA3lox gene had integrated at the PDA1 locus on chromosome V by homologous recombination (gene replacement), was selected and used in all co-cultivation experiments.

Yeast Co-Cultivation Experiments

*Agrobacterium* strains expressing the cre or cre-fusion gene were grown overnight at 29° C. in 5 ml MM (Hooykaas et al. (1979) J. Gen. Microbiol., 110, 99-109) supplemented with spectinomycin (250 µg/ml) and, in case a pRL662-based plasmid was present, also with gentamycin (40 µg/ml). Cells were harvested and diluted at an A600 of 0.25 in 5 ml induction medium (IM: MM salts and 40 mM 2-(N-morpholino) ethanesulfonic acid (MES), pH 5.3, 10 mM glucose, 0.5% (w/v) glycerol and 200 µM AS). The cells were then grown for 5 hours at 28° C.

*S. cerevisiae* strain LBY2 was grown overnight at 30° C. in 10 ml YPD medium (Sherman (1991) Methods Enzymol., 194, 3-21). Cells were diluted 1:10 in fresh 100 ml YPD medium and grown for 5 hours at 30° C. The cells were subsequently washed with and resuspended in 500 µl IM. 100 µl of the *Agrobacterium* and *Saccharomyces* cultures were mixed 1:1, and the mixture was placed on 0.45 µm cellulose nitrate filters on IM medium containing 5 mM glucose and the amino acids leucine and uracil at a concentration of 30 mg/l. To prevent loss of pRL662, gentamycin was added to the medium. After 6 days of co-cultivation at 22° C., the mixture was resuspended in 2 ml NaCl solution (9g/l) and 100 µl aliquots were plated out on solid MY medium supplemented with leucine, uracil, 200 µM cefotaxime and 0.1% fluoro-orotic acid (FOA). Ura⁻ colonies were selected after 4 days growth at 30° C. The output number of *Agrobacterium* cells was determined on solid LC medium supplemented with spectinomycin or gentamycin. The output number of *Saccharomyces* cells was determined on solid MY medium with cefotaxime and the amino acids leucine and uracil.

PCR Analysis

The method used for isolation of chromosomal DNA for PCR analysis and the protocol for the PCR reaction were described earlier (Vergunst et al., Plant Mol. Biol. 38 (1998), 393-406). As primers (a and b in FIG. 1) for the analysis of kanamycin-resistant calli and plants use was made of:

a) 5'-GAACTCGCCGTAAAGACTGGCG-3' (SEQ ID NO:17) annealing in the 35S promoter region (pDE35S in FIG. 1); and b) 5'-GCGCTGACAGCCGGAACACG-3' (SEQ ID NO:18) annealing in the nptII coding sequence (see FIG. 1). Primers used for plasmid construction are mentioned in detail.

Results

To show that *Agrobacterium* transfers fusion proteins into recipient plant cells, a recombination assay was used that allows the detection of the transport of the Cre recombinase. To this end, in experiments using *Arabidopsis* as host cells, the plant cell nucleus contained a DNA segment which, after specific deletion by Cre, results in a selectable kanamycin-resistance trait. This substrate for Cre recombination (pSDM3043, FIG. 1) was transferred by *Agrobacterium*-mediated transformation into the genome of *Arabidopsis* by means of selection for resistance to phosphinothricin. The transgenic plants were sensitive to kanamycin. However, the Cre-mediated recombination between two in tandem oriented lox sites results in excision of the intervening DNA segment and in the activation of the nptII gene by translational fusion of the 35S promoter region including the ATG start codon and an N-terminal coding part (determined by the lox sequence) with the coding region of nptII. This fusion leads to kanamycin resistance. Thus, only cells in which a Cre-mediated recombination event has taken place survive on the selective medium. A plant line was isolated, comprising a single locus of the excision substrate and whose excision efficiency (as measured by the number of kanamycin-resistant calli due to Cre activity) was comparable to that of the efficiency of *Agrobacterium*-mediated transformation. This was tested by co-cultivation of the plant line with an *Agrobacterium* strain carrying a binary vector with a T-DNA harboring the cre gene driven by a strong promoter sequence (LBA1115-pSDM3088). The selected excision line was used in further assays to prove direct protein transport, including the Cre-recombinase, from *Agrobacterium* to plant cells. To this end, Cre-recombinase was expressed under control of the vir-induction system in *Agrobacterium*, either alone or as an N-terminal or C-terminal fusion with VirF or VirE2, respectively. Expression of the fusion proteins in *Agrobacterium* was tested by immunoblot analysis (data not shown). Recombination activity of the fusion proteins was assayed by measuring the ability to induce an excision event in plasmid pSDM3043, which plasmid was introduced into the relevant bacterial strains in order to test this effect (data not shown).

After co-cultivation of the above-mentioned plant cells with the *Agrobacterium*-strains LBA1010, LBA1100, LBA1149, or LBA2561, or with a derivative of these strains harboring a plasmid expressing Cre-recombinase (the cre control plasmid), at most one single survivor was found on a selective medium. Thus, the same number of kanamycin-resistant calli ("the background") was obtained during co-cultivation with strains which do not express Cre as during co-cultivation with *Agrobacterium* strains which do express Cre-recombinase. Thus, we conclude that bacterially expressed Cre-recombinase is not transferred to plant cells.

The results were, however, totally different when experiments were done with *Agrobacterium* cells expressing fusion proteins between Cre and VirE2 or VirF. *Agrobacterium* strains were used (both wild type as well as mutants for the respective Vir protein) which express either C-terminal or N-terminal fusions of Cre with VirE2 and VirF, respectively. It was found that the fusion at the N-terminal region of the Vir protein (Cre::VirE2; NLS::Cre::VirF), but not at the C-terminal end (VirE2::Cre; NLS::VirF::Cre), was highly efficient in producing kanamycin-resistant calli. No difference was observed whether the Cre::VirF-fusion was expressed from the helper plasmid (LBA2561::NLS::cre::virF) or from plasmid pRL662 (LBA2561, pRL662 NLS::cre::virF). Co-cultivation of *Agrobacterium* strains (both wild type and virF mutant) expressing a Cre::VirF-fusion with a deletion of the 42 N-terminal amino acids of virF (NLS::Cre::VirFΔ1-126) resulted in kanamycin-resistant calli being obtained at a significantly higher frequency. Co-cultivation of a strain expressing a fusion protein between the last 37 C-terminal amino acids of VirF and Cre (NLS::Cre::VirFΔ1-498) resulted in comparable high numbers of kanamycin-resistant calli.

As controls, strains harboring the fusion plasmids NLS::cre::virFΔ1-126 and cre::virE2 were co-cultivated with wild type *Arabidopsis* C24 root explants, but as expected, these did not result in kanamycin-resistance due to the absence of the excision locus.

PCR-analysis proved that kanamycin resistance was indeed caused by the predicted Cre-mediated excision event. PCR analysis on DNA isolated from the excision line 3043 resulted in a fragment of 2.3 kb (see FIG. 1), whereas in DNA samples isolated from kanamycin-resistant calli which were obtained after co-cultivation of strains expressing cre::virE2 and NLS::cre::virF, a 0.7 kb fragment is obtained. To exclude contamination with a T-DNA vector expressing cre, a PCR analysis was performed with primers annealing in the cre coding region. As expected, no fragment was detected.

PCR analysis of the few calli obtained from the control experiments (including those from experiments in which cultivation took place with an *Agrobacterium* strain not harboring a cre gene) showed that these were partly the result of an excision, possibly due to homologous recombination between the lox sites and partly due to continuing growth of sensitive plants on the selection medium ("escapes"). In the latter case, the 2.3 kb fragment was detected, and not the 0.7 kb fragment indicating excision. All these results thus show that *Agrobacterium* can introduce Cre-recombinase into plant cells, but only when expressed as a fusion protein attached to the N-terminus of VirE2 or VirF. The efficiency of obtaining kanamycin-resistant calli after co-cultivation of plant line 3043 with the *Agrobacterium* strains expressing fusions of Cre with 161 or 37 C-terminal amino acids of VirF shows that there must be a transport domain in the last 37 C-terminal amino acids of VirF. In addition, a fusion protein between the C-terminal 20 amino acids of VirF Cre was still transported, but with lower efficiency.

In view of the in planta function of VirE2, virF and VirD2 shown before, the three invariant amino acids (RPR-motif) in the C-terminus of VirF, VirE2 and VirD2 suggest the importance of these amino acids for the transport of the Vir proteins to the plant, using the VirB/VirD4 system (see later). Mutation of one of the R residues in this motif leads to a decrease in transport efficiency, but when the P residue in a residue chosen from A, Q, V and S was changed, the transport activity remained intact. To gain further insight into the translocation signal, mutagenesis of the C-terminus of VirFΔ1-126 was performed, according to Sawano and Miyawaki (2000, NAR 28, e78). The 18 C-terminal amino acids were independently changed into alanine residues (D185A, R187A, E189A, M191A, S192A, D194A, R195A, P196A, R197A, S198A, T199A, R200A, G201A and L202A). The mutant fusion proteins were assayed for efficiency of transport in *Arabidopsis* excision line 3043. Data from 2 representative experiments are shown in FIG. 3.

Figure 4:
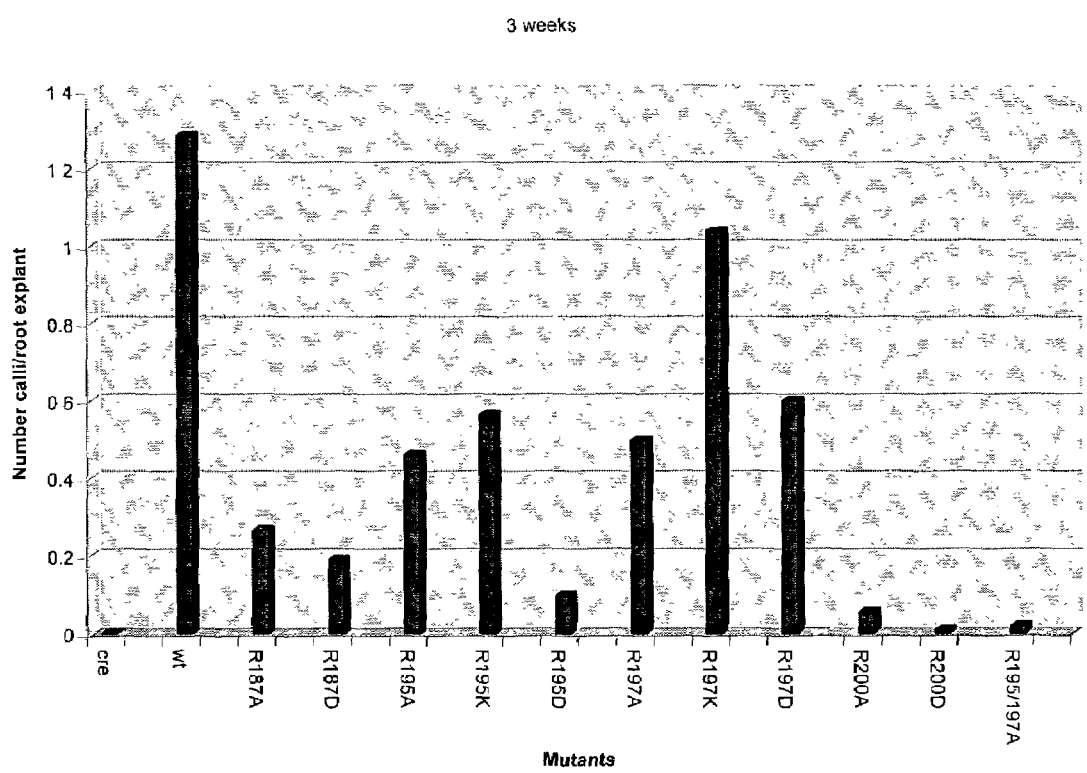
FIG. 4 Analysis of transport of Cre::virF fusion proteins into *Arabidopsis* excision line 3043. Cre: LBA1100 containing pSDM3147, wt: LBA1100 constaining pSDM3155 (Cre::virFdel1-126 wt), R187A, R187D, R195A, R195K, R195D, R197A, R197K, R197D, R200A, R200D, R195/197A: Single point mutations in cre::virFdel1-126.

Clearly, most single amino acid mutations have no significant impact on the efficiency of detection of transport. However, mutation of either of the arginine residues R187, R195, R197 or R200 resulted in a reduced efficiency with which transport is detected. R187 and R200 show to be most important, but not essential because transport can still be detected. A closer look was taken at the R residues by changing these amino acids into the basic lysine (K), or acidic aspartate (D) (FIG. 4). R187D, R195K, R195D, R197K, R197D, R200D, and R195/197A have been tested, and in these experiments, it appeared that after changing the arginine residue into a lysine residue, still considerable activity was left (see, FIG. 4).

In the present experiments, transport of the fusion proteins, detected as kanamycin resistance after co-cultivation with plant line 3043, occurs independent of co-transfer of T-DNA. This implies an important application of the protein transport system, namely, the possibility of effecting a change in cells in the absence of T-DNA. In addition, however, transfer may also occur in the presence of T-DNA (that may or may not be oncogenic), which broadens the applicability of the system. Possible application may be site-directed integration of T-DNA in the genome of the recipient cell by means of cotransport of a recombinase that is expressed as a fusion protein in the same or in cotransforming bacteria.

To determine which of the virulence functions are essential for protein transport, NLS::cre::virFΔ1-126 and cre::virE2 were transferred into a set of vir mutants, listed in Table 1.

Co-cultivation of the excision line with the virA, virB, virG and virD4 mutants, which harbor the fusion plasmids, did not result in Cre-mediated excision, whereas virC, virD1/D2, virF and virE2 mutants resulted in calli with efficiencies comparable to the efficiencies of the wild type. Thus, we can conclude that, in this model system wherein VirA and VirG are responsible for forming VirB and VirD4, expression of vir genes through the regulators VirA and VirG is necessary for transport. The virB genes and virD4, determining the type IV secretion channel (B-complex) and the coupling factor (VirD4), are essential. The occurrence of virB and virD4 homologs in other systems (for example, O'Callaghan et al., Mol. Microbiol. 33 (1999), 1210-1220) makes it possible to construct similar protein transport systems in *Agrobacterium* and other microorganisms based on these homologous systems. The other virulence genes, including those coding for the transported proteins VirD2, VirE2 and VirF, appeared not to be necessary for transport of the fusion proteins.

Figure 5:
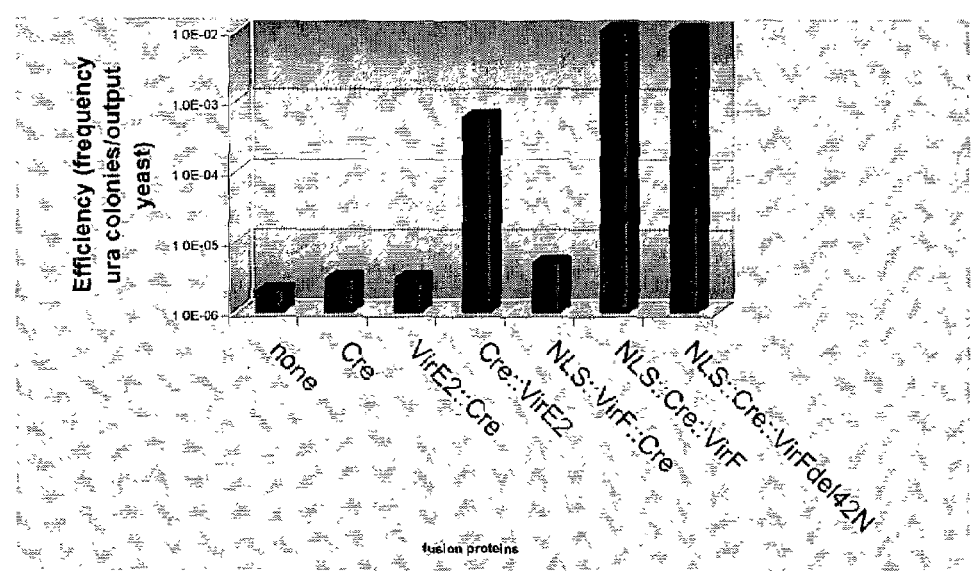
FIG. 5 Analysis of protein transport from *Agrobacterium* into yeast strain LBY2. Strain LBA1100 containing no plasmid (none), pSDM3147 (cre), pSDM3148 (virE2::Cre), pSDM3129 (Cre::virE2), pSDM3153 (NLS::virF::cre), pSDM3154 (NLS::cre::virF) or pSDM3155 (NLS::cre:: virF::del1-126=42N). Efficiency is calculated as the number of yeast colonies growing on medium containing FOA/ output number of yeast cells.
Figure 6:
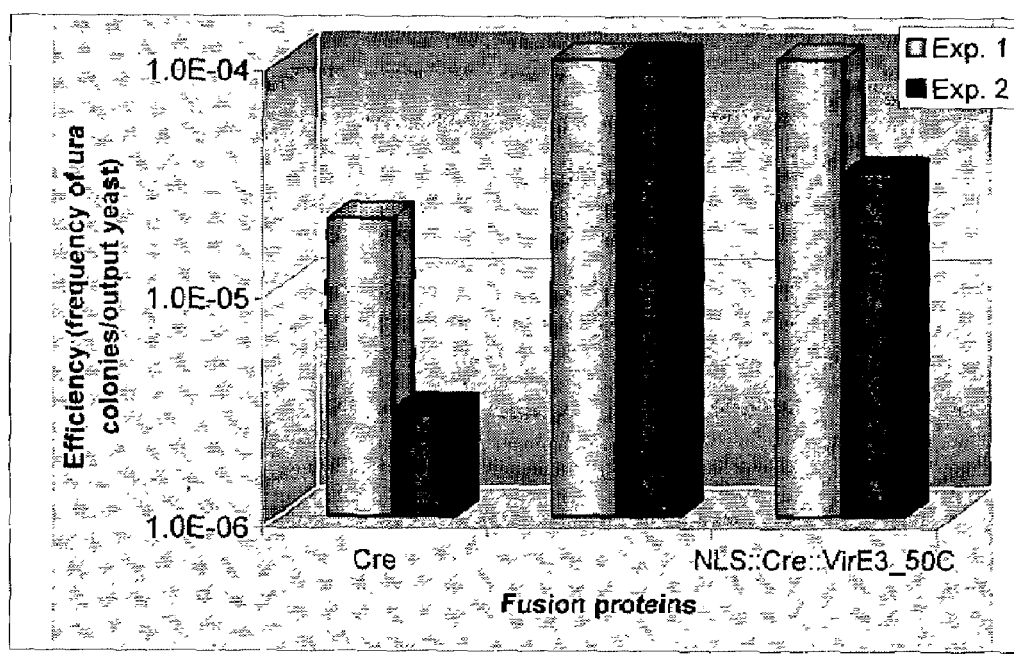
FIG. 6 Analysis of VirE3 protein transport from *Agrobacterium* into yeast in two independent experiments. Strain LBA1100 containing pSDM3147 (cre), or a plasmid expressing an NLS::cre::virE3, or NLS::cre::virE3 (50 C terminal amino acids). Efficiency is calculated as the number of yeast colonies growing on medium containing FOA/ output number of yeast cells.

To prove that under the same conditions *Agrobacterium* will transfer fusion proteins into other eukaryotic cells, a recombination assay similar to the one described above was performed with yeast cells (FIG. 2). The yeast cells do not grow in the presence of 5-fluoro uracil, unless a recombinase removes the gene present between lox sites, which gene encodes a protein that converts 5-fluoro uracil into a substance that is toxic for the yeast cell. The recombinase was introduced as a fusion protein. As expected, the thus-treated yeast became resistant to 5-fluoro uracil (see, FIG. 5). In these experiments, the transport of the recombinase by means of the C-terminus of VirE2 and VirF was confirmed and, in addition, the transport via the C-termini of VirE3 (see, FIG. 6) and the MobA protein of the incQ plasmid RSF1010 was shown (results not shown). In the VirE3 protein, the RPR sequence is also present in the C-terminus, in VirD5 an RDR sequence is present and in MobA the RQR sequence is present. In addition, transport of the 50 C-terminal amino acids of VirD5 was confirmed into plants. Alignment of the C-termini of VirE2, VirF, VirE3, VirD2, VirD5 and MobA (see Table 2) shows that the C-terminus is hydrophilic.

```
                                               SEQ ID NO:1
Amino acid sequence of virF_15955(1-609)
Universal code
Total number of amino acids: 202, MW = 22394
Max ORF: 1-606, 202 AA, MW = 22394
ORIGIN
      1   MRNSSLRDAS GSNDAQVPHK

21   TELLNLPDHV LTEVAKRLAT

41   NNPVESAENI ANFSKSHRFT

61   RDAVRTEPLE KFSSRLKILS

81   RNAKLLSHAV RHAATLPDGE

101   QLSEAQLSQM RSEVATRPVL

121   GVAYTHQDGQ PEERLSGNHL

141   DHKINNIPNL VFNVAEPIMF

161   NEISALEVMA EVRPIARSIK

181   TAHDDARAEL MSADRPRSTR

201   GL*
                                               SEQ ID NO:2
Amino acid sequence of VirD2_pTi15955(1-1275)
Universal code
Total number of amino acids:424, MW = 47476
Max ORF: 1-1272, 424 AA, MW = 47476
ORIGIN
      1   MPDRAQVIIR IVPGGGTKTL

21   QQIINQLEYL SRKGKLELQR

41   SARHLDIPVP PDQIRELAQS

61   WVTEAGIYDE SQSDDDRQQD

81   LTTHIIVSFP AGTDQTAAYE

101   ASREWAAEMF GSGYGGGRYN

121   YLTAYHVDRD HPHLHVVVNR

141   RELLGHGWLK ISRRHPQLNY

161   DGLRKKMAEI SLRHGIVLDA

181   TSRAERGIAE RPITYAEHRR

201   LERMQAQKIQ FEDTDFDETS

221   PEEDRRDLSQ SFDPFRSDPS

241   TGEPDRATRH DKQPLEQHAR

261   FQESAGSSIK ADARIRVSLE

281   SERSAQPSAS KIPVIGHFGI

301   ETSYVAEASV RKRSGIFGTS

321   RPVTDVAMHT VKRQQRSKRR

341   NDEEAGPSGA NRKGLKAAQV

361   DSEANVGEQD TRDDSNKAAD

381   PVSASIGTEQ PEASPKRPRD

401   RHDGELGGRK RARGNRRDDG

421   RGGT*
                                               SEQ ID NO:3
Amino acid sequence of virE2_pTi15955(1-1602)
Universal code
Total number of amino acids: 533, MW = 60502
Max ORF: 1-1599, 533 AA, MW = 60502
ORIGIN
      1   MDLSGNEKSR PWKKANVSSS

21   TISDIQMTNG ENLESGSPTR

41   TEVLSPRLDD GSVDSSSSLY

61   SGSEHGNQAE IQKELSALFS

81   NMSLPGNDRR PDEYILVRQT

101   GQDAFTGIAK GNLDHMPTKA

121   EFNACCRLYR DGAGNYYPPP

141   LAFDKISVPA QLEETWGMME

161   AKERNKLRFQ YKLDVWNHAH

181   ADMGITGTEI FYQTDKNIKL

201   DRNYKLRPED RYVQTERYGR

221   REIQKRYQHE LQAGSLLPDI

241   MIKTPKNPIH FVYRFAGDNY

261   ANKQFSEFEH TVKRRYGGET

281   EIKLKSKSGI MHDSKYLESW

301   ERGSADIRFA EFVGENRAHN

321   RQFPTATVNM GQQPDGQGGL

341   TRDRHVSVEF LMQSAPNSPW

361   AQALKKGELW DRVQLLARDG

381   NRYLSPHRLE YSDPEHFTEL

401   MNRVGLPASM GRQSHAASIK

421   FEKFDAQAAV IVINGPELRD

441   IHDLSPENLQ NVSTKDVIVA

461   DRNENGQRTG TYTSVAEYER

481   LQLRLPADAA GVLGEAADKY

501   SRDFVRPEPA SRPISDSRRI

521   YESRPRSQSV NSF*
                                               SEQ ID NO:4
Amino acid sequence of virE3-pTi15955(1-2019)
Universal code
Total number of amino acids: 672, MW = 75584
Max ORF: 1-2016, 672 AA, MW = 75584
ORIGIN
      1   MVSTTKKSFA KSLTADMRRS

21   AQRVVEQMRK ALITEEEALK

41   RQTRLESPDR KRKYAADMAI

61   VDKLDVGFRG EIGYKILGNK

81   RLRVDNPKEL TREHGRLRKT

101   KTVLKRNPVT QEVYLGLHER

121   KSWLSVSSHL YAADGTLRMK
```

-continued

```
141  HVKYKDGRFE ERWERDENGD
161  LIRTRYANRG RLFQPVSEKM
181  GAPYRSGPDN RLYRDLTRQN
201  GFRRETFERD DQGNLERIGS
221  NHVGFSKISV KAANRQTSQT
241  KIQKLGGAFN KSFRSLLDKE
261  GNELGRDILS HRRLYNKRSA
281  VYDEATGQLK SAKHTFGKIY
301  RSETDYLSAG LKKVSKKILG
321  VTVYRKFAAL SERESEAERL
341  RSFESGAHRQ IWQERAATPG
361  SPPSESDDIH FAQQSHLAKA
381  NSDHVEADVM RVTDQHIDVA
401  GQTSSSRQRN LEERLDSQSR
421  YKPANMLLSD PDLRADGPRP
441  YEGLAELTLR RDNESDGHKE
461  NDQRLRHFLQ PEPLVLPHPG
481  SPEITKVFGS RGEPLHPSGT
501  LHTAVGETAC EAPVMSSSLD
521  NHQPAPGQQE LLSLLHNAPA
541  PVSVAIHDEQ ERLAGEAPGG
561  SFRGSSGRTS SMSESIFDED
581  VQSHLVRDYS INPTNGFIDP
601  QSLFGGPDLS RGPKSGPEIP
621  SEDYHLSASE QENLLNQLLS
641  VPLPIPSPKP KSARSMIFEG
661  SRPRERSTSR GF*
```

SEQ ID NO:5
Derived amino acid sequence of
RSF1010_mobA(1-2130)
Universal code
Total number of amino acids: 709, MW = 77847

```
  1  MAIYHLTAKT GSRSGGQSAR
 21  AKADYIQREG KYARDMDEVL
 41  HAESGHMPEF VERPADYWDA
 61  ADLYERANGR LFKEVEFALP
 81  VELTLDQQKA LASEFAQHLT
101  GAERLPYTLA IHAGGGENPH
121  CHLMISERIN DGIERPAAQW
141  FKRYNGKTPE KGGAQKTEAL
161  KPKAWLEQTR EAWADHANRA
181  LERAGHDARI DHRTLEAQGI
201  ERLPGVHLGP NVVEMEGRGI
221  RTDRADVALN IDTANAQIID
241  LQEYREAIDH ERNRQSEEIQ
261  RHQRVSGADR TAGPEHGDTG
281  RRSPAGHEPD PAGQRGAGGG
301  VAESPAPDRG GMGGAGQRVA
321  GGSRRGEQRR AERPERVAGV
341  ALEAMANRDA GFHDAYGGAA
361  DRIVALARPD ATDNRGRLDL
381  AALGGPMKND RTLQAIGRQL
401  KAMGCERFDI GVRDATTGQM
421  MNREWSAAEV LQNTPWLKRM
441  NAQGNPVYIR PAEQERHGLV
461  LVDDLSEFDL DDMKAEGREP
481  ALVVETSPKN YQAWVKVADA
501  AGGELRGQIA RTLASEYDAD
521  PASADSRHYG RLAGFTNRKD
541  KHTTRAGYQP WVLLRESKGK
561  TATAGPALVQ QAGQQIEQAQ
581  RQQEKARRLA SLELPERQLS
601  RHRRTALDEY RSEMAGLVKR
621  FGDDLSKCDF IAAQKLASRG
641  RSAEEIGKAM AEASPALAER
661  KPGHEADYIE RTVSKVMGLP
681  SVQLARAELA RAPAPRQRGM 701 DRGGPDFSM*
```

SEQ ID NO:6
Translation of VirD5_pTi15955(1-2502)
Universal code
Total amino acid number: 833, MW = 92859

```
  1  MTGKSKVHIR SSADTLPDGS
 21  ITAPFSTGLS GDQADASFEA
 41  QTDYSQSTSV SFTYDGVKLG
 61  PAERAAYENW CEPGRPTWKD
 81  LIIKARVDPI DDVIWLRDLE
101  EDTPSTFRYE GMPLGLGERK
121  AYENWQEDAQ PTWEDLVVSA
141  RMTELGRPHG ITGEYTSLAG
161  SKNTSSISLK RKRSNLTDDE
181  NSSGSFSYDG MKLGEAERSA
201  YGDWAEAEPP TWKDLVLRAR
221  VSSINDSAWL FDSQTSSSSF
241  EYNGVPLGEP ERQALRQWQG
261  DAQPTWEDLV VNARMAELCH
281  AGWIEGQKGC FEKRGEALHA
```

-continued

| | |
|---|---|
| 301 | SERGSQRPIV QRTDSSDSFL |
| 321 | YDGRRLGAPE RTAYERWSKR |
| 341 | ERPTWEDLIL DAHQARIESD |
| 361 | AVTTQAIGQS SSLVFLYEGK |
| 381 | SLGCREREAY EKWRQPAQPR |
| 401 | WQNLVVNARL AELDPSVWIA |
| 421 | DERDPLDDGD ALGRPSYTSL |
| 441 | TDRSDVPLDD QSIYHRSDLV |
| 461 | REQVSESSQK QFAACSESET |
| 481 | IPVSWFTASG LDANNTENIA |
| 501 | ASDPVDGTGG VKRLGSKSDR |
| 521 | TVTASIHDVN SSTKRLLLNE |
| 541 | FGLEAPRPSP EKTVRLRSDN |
| 561 | IGTYGSRRNE RMRLATETGA |
| 581 | YESEHIFGFK AVHDTARATK |
| 601 | EGRRLERPMP AYLEYKGLHR |
| 621 | QHVGTGRGRT KLVGRGWPDD |
| 641 | TSYRSDQRAT LSDPVARSEG |
| 661 | ATASNGYQLN QLGYAHQLAS |
| 681 | DGLQSESPDG VALPIQVATT |

-continued

| | |
|---|---|
| 701 | SYNYTVSRDP VLVPPDKNEA |
| 721 | PQLLHLGPRG QTEAVLARET |
| 741 | ALTGKWPTLE REQQVYREFL |
| 761 | ALYDVKKDLE AKSVGVRQKK |
| 781 | KEVSSALDRT ARLIITSPSK |
| 801 | ARSEAETEKA IDELDDRRVY |
| 821 | DPRDRAQDKA FKR* |

TABLE 2

Hand-alignment of C-terminal peptides virF EVMAEVRPIARSIKTAH DDARAELMSADRPRSTRGL* (SEQ ID NO:25)

virE2 AADKYSRDFVRPEPASR PISDSRRIYESRPRSQSVNSF* (SEQ ID NO:26)

virE3 LLNQLLSVPLPIPSPKP KSARSMIFEGSRPRERSTSRGF* (SEQ ID NO:27)

VirD2 SASIGTEQPEASPKRPR DRHDGELGGRKRARGNRRDDGRGGT* (SEQ ID NO:28)

VirD5 ITSPSKARSEAETEKAI DELDDRRVYDPRDRAQDKAFKR* (SEQ ID NO:29)

mobA YIERTVSKVMGLPSVQL ARAELARAPAPRQRGMDRGGPDFSM* (SEQ ID NO:30)

What is claimed is:

1. A method of effecting a change in a cell, wherein a bacterial transfer system is contacted with the cell to be changed, said bacterial transfer system including a protein transport system comprising a pore comprising a VirB protein complex and a VirD4 coupling factor, wherein the bacterial transfer system comprises a fusion protein or is capable of making a fusion protein which is introduced into the cell to be changed using the protein transport system, the method comprising:

introducing the fusion protein into the cell to be changed, which fusion protein comprises a first part A and a second part B, the first part A and second part B derived from different proteins, wherein;

the first part A comprises an oligopeptide means for transporting part B through said pore, said means having the 20 most C-terminal amino acids of a bacterial protein transported through said pore, and at least two arginine or lysine amino acids and at least 50% hydrophilic or neutral amino acids; and the second part B comprises a polypeptide capable of exerting a cell-changing activity in the cell to be changed, wherein a C-terminal end of the polypeptide of the second part B is linked to an N-terminal end of the first part A, with the proviso that if the fusion protein comprises a first part A derived from VirE2, the fusion protein does not comprise the 84 N-terminal amino acids of VirE2; and effecting a change in the cell.

2. The method according to claim 1, wherein the fusion protein is formed by expression in the bacterial transfer system.

3. The method according to claim 1, wherein the fusion protein is introduced into the cell to be changed without introducing a DNA- or RNA-sequence.

4. The method according to claim 2, wherein the fusion protein is introduced into the cell to be changed without introducing a DNA- or RNA-sequence.

5. The method according to claim 1, wherein the introduced fusion protein possesses a recombinase activity.

6. The method according to claim 2, wherein the introduced fusion protein possesses a recombinase activity.

7. The method according to claim 3, wherein the introduced fusion protein possesses a recombinase activity.

8. The method according to claim 4, wherein the introduced fusion protein possesses a recombinase activity.

9. The method according to claim 1, wherein a bacterium from the class of Rhizobiaceae is used as the transfer system.

10. The method according to claim 1, wherein the cell to be modified is selected from the group consisting of i) a plant cell; ii) a yeast cell; and iii) a fungal cell.

11. A vector that codes for a fusion protein BA, for use in a bacterial protein transport system comprising a pore and the fusion protein BA, wherein the pore comprises a VirB protein complex and a VirD4 coupling factor, the vector comprising:

a nucleic acid sequence coding for the fusion protein BA, wherein the nucleic acid sequence comprises a 5' first part A linked to a 3' second part B, wherein the first part A and the second part B encodes an amino acid sequence and the amino acid sequence of part A and part B are derived from different proteins, wherein:

the first part A encodes an oligopeptide means for transporting the 3' second part B through the pore, said means comprising at least a 20 most C-terminal amino acid portion of a bacterial protein transported through said pore, and comprises at least two arginine or lysine amino acids and having at least 50% hydrophilic or neutral amino acids; and the second part B encodes a polypeptide capable of effecting a cell-modifying activity in a cell to be modified, with the proviso that if the nucleic acid sequence comprises a first part A encoding at least the 20 most C-terminal amino acid portion of VirE2, the nucleic acid sequence does not encode a 84 most N-terminal amino acid portion of VirE2.

12. A vector set, comprising one or more vectors coding for a bacterial protein transport system, wherein the bacterial protein transport system comprises a fusion protein and a pore comprising a VirB protein complex and a VirD4 coupling factor, wherein the fusion protein comprises:

a first amino acid sequence at an N-terminal end of the fusion protein and a second amino acid sequence at a C-terminal end of the fusion protein, wherein the first amino acid sequence and the second amino acid sequence of the fusion protein are derived from different proteins, the first amino acid sequence being capable of exercising a cell-modifying activity in a cell to be modified; and the second amino acid sequence comprising at least the 20 C-terminal amino acids of a bacterial protein, wherein the at least 20 C-terminal amino acids are a means for transporting the first amino acid sequence through the pore and comprises at least two arginine or lysine amino acids and at least 50% hydrophilic or neutral amino acids; with the proviso that if the at least 20 C-terminal amino acids are derived from VirE2, the fusion protein does not comprise a 84 most N-terminal amino acid region of VirE2.

13. The vector set of claim 12, wherein the second amino acid sequence comprises at least 20 amino acids selected from the group consisting of at least the 20 most C-terminal amino acids of VirF, VirD2, VirE2, VirE3, VirD5 and MobA.

14. The method according to claim 1, wherein the bacterial protein transported through said pore is selected from the group consisting of VirF, VirD2, VirE2, VirE3, VirD5 and MobA.

15. The vector of claim 11, wherein the bacterial protein transported through said pore is selected from the group consisting of VirF, VirD2, VirE2, VirE3, VirD5 and MobA.

16. The vector set of claim 12, wherein the bacterial protein transported through said pore is selected from the group consisting of VirF, VirD2, VirE2, VirE3, VirD5 and MobA.

* * * * *

UNITED STATES PATENT AND TRADEMARK OFFICE
CERTIFICATE OF CORRECTION

PATENT NO. : 7,314,737 B2  
APPLICATION NO. : 10/300666  
DATED : January 1, 2008  
INVENTOR(S) : Paul Jan J. Hooykaas, Annette Caroline Vergunst and Barbara Schrammeijer It is certified that error appears in the above-identified patent and that said Letters Patent is hereby corrected as shown below:

On the title page:
In ITEM (75) Inventors:   change "Annette Carolin Vergunst, Bussum (NL);" to --Annette Caroline Vergunst, Bussum (NL);--

In ITEM (73) Assignee:   change "Stichting voor de technische Watenschappen in Utrecht (NL);" to --Stichting voor de Technische Wetenschappen in Utrecht (NL);--

In the specification:
COLUMN 7, LINES 28,30   change "(5'-acgcgtcgactATCGCCATCTTCCAGCAGGCGC) (SEQ ID NO:3)" to --(5'-acgcgtcgact ATCGCCATCTTCCAGCAGGCGC) (SEQ ID NO:3)--

COLUMN 7, LINES 64,66   change "(5'-TCGACCGCGTAGCCAAAGCGTCAACAGCTTTcga (SEQ ID NO:7)" to --(5'-TCGACCGCGTAGCCAAAGCGTCAACAGCTTTcga) (SEQ ID NO: 7)--

UNITED STATES PATENT AND TRADEMARK OFFICE
CERTIFICATE OF CORRECTION

PATENT NO. : 7,314,737 B2
APPLICATION NO. : 10/300666
DATED : January 1, 2008
INVENTOR(S) : Paul Jan J. Hooykaas, Annette Caroline Vergunst and Barbara Schrammeijer It is certified that error appears in the above-identified patent and that said Letters Patent is hereby corrected as shown below:

In the specification (continued):

COLUMN 8, LINES 52,53 change "5'-gatctatcccggg<u>ctcgagg</u> (SEQ ID NO:14))" to --5'-gatctatcccggg<u>ctcgagg</u> (SEQ ID NO:14))--

Signed and Sealed this

Twenty-third Day of December, 2008

JON W. DUDAS
*Director of the United States Patent and Trademark Office*

SEQUENCE LISTING

<160> NUMBER OF SEQ ID NOS: 30

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: primer cre1
<220> FEATURE:
<221> NAME/KEY: misc_feature
<222> LOCATION: (1)..(22)

<400> SEQUENCE: 1
ggcagatctg tccaatttac tg                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: primer cre2
<220> FEATURE:
<221> NAME/KEY: misc_feature
<222> LOCATION: (1)..(22)

<400> SEQUENCE: 2
gataatcgcg aacatcttca gg                                              22

```
<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: primer cre6
<220> FEATURE:
<221> NAME/KEY: misc_feature
<222> LOCATION: (1)..(33)

<400> SEQUENCE: 3
acgcgtcgac tatcgccatc ttccagcagg cgc                    33

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: primer cre7
<220> FEATURE:
<221> NAME/KEY: misc_feature
<222> LOCATION: (1)..(26)

<400> SEQUENCE: 4
ccatcgattg atttacggcg ctaagg                            26

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: XhoI-StuI
      linker
<220> FEATURE:
<221> NAME/KEY: misc_feature
<222> LOCATION: (1)..(31)

<400> SEQUENCE: 5
tcgagatctt tctggcaatg agaaatccag g                      31

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: XhoI-StuI
      linker
<220> FEATURE:
<221> NAME/KEY: misc_feature
<222> LOCATION: (1)..(27)

<400> SEQUENCE: 6
cctggatttc tcattgccag aaagatc                           27

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: SalI/BglII
      linker
<220> FEATURE:
<221> NAME/KEY: misc_feature
<222> LOCATION: (1)..(34)

<400> SEQUENCE: 7
tcgaccgcgt agccaaagcg tcaacagctt tcga                   34

<210> SEQ ID NO 8
```

```
<211> LENGTH: 34
<212> TYPE: DNA
<213> ORGANISM: Artificial Sequence
<220> FEATURE:
<223> OTHER INFORMATION: Description of Artificial Sequence: SalI/BglII
      linker
<220> FEATURE:
<221> NAME/KEY: misc_feature
<222> LOCATION: (1)..(34)

<400> SEQUENCE: 8
gatctcgaaa gctgttgacg ctttggctac gcgg                              34

<210> SEQ ID NO 9
<211> LENGTH: 68
<212> TYPE: DNA
<213> ORGANISM: Artificial Sequence
<220> FEATURE:
<223> OTHER INFORMATION: Description of Artificial Sequence: sequence
      comprising NLS of simian virus 40
<220> FEATURE:
<221> NAME/KEY: misc_feature
<222> LOCATION: (1)..(68)

<400> SEQUENCE: 9
atcatggata aagcggaatt aattcccgag cctccaaaaa agaagagaaa ggtcgaattg    60
ggtaccgg                                                            68

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: BamHI/NsiI
      linker
<220> FEATURE:
<221> NAME/KEY: misc_feature
<222> LOCATION: (1)..(28)

<400> SEQUENCE: 10
gatccgaaat tcgagtttgc gtgatgca                                      28

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(21)

<400> SEQUENCE: 11
atccctaact tggtcttcaa c                                             21

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(29)

<400> SEQUENCE: 12
cttagatcta gaccgcgcgt tgatcgagg                                     29
```

```
<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: StuI/BglII
      linker
<220> FEATURE:
<221> NAME/KEY: misc_feature
<222> LOCATION: (1)..(16)

<400> SEQUENCE: 13
cctcgagccc gggata                                                        16

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: StuI/BglII
      linker
<220> FEATURE:
<221> NAME/KEY: misc_feature
<222> LOCATION: (1)..(20)

<400> SEQUENCE: 14
gatctatccc gggctcgagg                                                    20

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: primer F126
<220> FEATURE:
<221> NAME/KEY: misc_feature
<222> LOCATION: (1)..(27)

<400> SEQUENCE: 15
acgcgtcgac ctgtcgagtc ggctgag                                            27

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer
      pflF2
<220> FEATURE:
<221> NAME/KEY: misc_feature
<222> LOCATION: (1)..(20)

<400> SEQUENCE: 16
gaccagcaca cttagatacc                                                    20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(22)

<400> SEQUENCE: 17
gaactcgccg taaagactgg cg                                                 22

<210> SEQ ID NO 18
```

-continued

```
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(20)

<400> SEQUENCE: 18
gcgctgacag ccggaacacg                                                  20

<210> SEQ ID NO 19
<211> LENGTH: 202
<212> TYPE: PRT
<213> ORGANISM: Artificial Sequence
<220> FEATURE:
<223> OTHER INFORMATION: Description of Artificial Sequence: sequence of
      virF_15955 (1-609)
<220> FEATURE:
<221> NAME/KEY: SITE
<222> LOCATION: (1)..(202)

<400> SEQUENCE: 19
```

Met Arg Asn Ser Ser Leu Arg Asp Ala Ser Gly Ser Asn Asp Ala Gln
 1               5                  10                  15

Val Pro His Lys Thr Glu Leu Leu Asn Leu Pro Asp His Val Leu Thr
            20                  25                  30

Glu Val Ala Lys Arg Leu Ala Thr Asn Asn Pro Val Glu Ser Ala Glu
        35                  40                  45

Asn Ile Ala Asn Phe Ser Lys Ser His Arg Phe Thr Arg Asp Ala Val
    50                  55                  60

Arg Thr Glu Pro Leu Glu Lys Phe Ser Ser Arg Leu Lys Ile Leu Ser
65                  70                  75                  80

Arg Asn Ala Lys Leu Leu Ser His Ala Val Arg His Ala Ala Thr Leu
                85                  90                  95

Pro Asp Gly Glu Gln Leu Ser Glu Ala Gln Leu Ser Gln Met Arg Ser
            100                 105                 110

Glu Val Ala Thr Arg Pro Val Leu Gly Val Ala Tyr Thr His Gln Asp
        115                 120                 125

Gly Gln Pro Glu Glu Arg Leu Ser Gly Asn His Leu Asp His Lys Ile
    130                 135                 140

Asn Asn Ile Pro Asn Leu Val Phe Asn Val Ala Glu Pro Ile Met Phe
145                 150                 155                 160

Asn Glu Ile Ser Ala Leu Glu Val Met Ala Glu Val Arg Pro Ile Ala
                165                 170                 175

Arg Ser Ile Lys Thr Ala His Asp Asp Ala Arg Ala Glu Leu Met Ser
            180                 185                 190

Ala Asp Arg Pro Arg Ser Thr Arg Gly Leu
        195                 200

```
<210> SEQ ID NO 20
<211> LENGTH: 424
<212> TYPE: PRT
<213> ORGANISM: Artificial Sequence
<220> FEATURE:
<223> OTHER INFORMATION: Description of Artificial Sequence: sequence of
      VirD2_pTi15955 (1-1275)
<220> FEATURE:
<221> NAME/KEY: SITE
<222> LOCATION: (1)..(424)

<400> SEQUENCE: 20
```

-continued

```
Met Pro Asp Arg Ala Gln Val Ile Ile Arg Ile Val Pro Gly Gly Gly
 1               5                  10                  15

Thr Lys Thr Leu Gln Gln Ile Ile Asn Gln Leu Glu Tyr Leu Ser Arg
             20                  25                  30

Lys Gly Lys Leu Glu Leu Gln Arg Ser Ala Arg His Leu Asp Ile Pro
         35                  40                  45

Val Pro Pro Asp Gln Ile Arg Glu Leu Ala Gln Ser Trp Val Thr Glu
     50                  55                  60

Ala Gly Ile Tyr Asp Glu Ser Gln Ser Asp Asp Arg Gln Gln Asp
 65                  70                  75                  80

Leu Thr Thr His Ile Ile Val Ser Phe Pro Ala Gly Thr Asp Gln Thr
                 85                  90                  95

Ala Ala Tyr Glu Ala Ser Arg Glu Trp Ala Ala Glu Met Phe Gly Ser
            100                 105                 110

Gly Tyr Gly Gly Gly Arg Tyr Asn Tyr Leu Thr Ala Tyr His Val Asp
            115                 120                 125

Arg Asp His Pro His Leu His Val Val Asn Arg Arg Glu Leu Leu
    130                 135                 140

Gly His Gly Trp Leu Lys Ile Ser Arg Arg His Pro Gln Leu Asn Tyr
145                 150                 155                 160

Asp Gly Leu Arg Lys Lys Met Ala Glu Ile Ser Leu Arg His Gly Ile
                165                 170                 175

Val Leu Asp Ala Thr Ser Arg Ala Glu Arg Gly Ile Ala Glu Arg Pro
                180                 185                 190

Ile Thr Tyr Ala Glu His Arg Arg Leu Glu Arg Met Gln Ala Gln Lys
            195                 200                 205

Ile Gln Phe Glu Asp Thr Asp Phe Asp Glu Thr Ser Pro Glu Glu Asp
        210                 215                 220

Arg Arg Asp Leu Ser Gln Ser Phe Asp Pro Phe Arg Ser Asp Pro Ser
225                 230                 235                 240

Thr Gly Glu Pro Asp Arg Ala Thr Arg His Asp Lys Gln Pro Leu Glu
                245                 250                 255

Gln His Ala Arg Phe Gln Glu Ser Ala Gly Ser Ser Ile Lys Ala Asp
            260                 265                 270

Ala Arg Ile Arg Val Ser Leu Glu Ser Glu Arg Ser Ala Gln Pro Ser
        275                 280                 285

Ala Ser Lys Ile Pro Val Ile Gly His Phe Gly Ile Glu Thr Ser Tyr
    290                 295                 300

Val Ala Glu Ala Ser Val Arg Lys Arg Ser Gly Ile Phe Gly Thr Ser
305                 310                 315                 320

Arg Pro Val Thr Asp Val Ala Met His Thr Val Lys Arg Gln Gln Arg
                325                 330                 335

Ser Lys Arg Arg Asn Asp Glu Glu Ala Gly Pro Ser Gly Ala Asn Arg
            340                 345                 350

Lys Gly Leu Lys Ala Ala Gln Val Asp Ser Glu Ala Asn Val Gly Glu
        355                 360                 365

Gln Asp Thr Arg Asp Asp Ser Asn Lys Ala Ala Asp Pro Val Ser Ala
    370                 375                 380

Ser Ile Gly Thr Glu Gln Pro Glu Ala Ser Pro Lys Arg Pro Arg Asp
385                 390                 395                 400

Arg His Asp Gly Glu Leu Gly Gly Arg Lys Arg Ala Arg Gly Asn Arg
                405                 410                 415
```

Arg Asp Asp Gly Arg Gly Gly Thr
              420

<210> SEQ ID NO 21
<211> LENGTH: 533
<212> TYPE: PRT
<213> ORGANISM: Artificial Sequence
<220> FEATURE:
<223> OTHER INFORMATION: Description of Artificial Sequence: sequence of
      virE2_pTi15955 (1-1602)
<220> FEATURE:
<221> NAME/KEY: SITE
<222> LOCATION: (1)..(533)

<400> SEQUENCE: 21

Met Asp Leu Ser Gly Asn Glu Lys Ser Arg Pro Trp Lys Lys Ala Asn
 1               5                  10                  15

Val Ser Ser Ser Thr Ile Ser Asp Ile Gln Met Thr Asn Gly Glu Asn
                20                  25                  30

Leu Glu Ser Gly Ser Pro Thr Arg Thr Glu Val Leu Ser Pro Arg Leu
            35                  40                  45

Asp Asp Gly Ser Val Asp Ser Ser Ser Leu Tyr Ser Gly Ser Glu
    50                  55                  60

His Gly Asn Gln Ala Glu Ile Gln Lys Glu Leu Ser Ala Leu Phe Ser
 65                  70                  75                  80

Asn Met Ser Leu Pro Gly Asn Asp Arg Arg Pro Asp Glu Tyr Ile Leu
                85                  90                  95

Val Arg Gln Thr Gly Gln Asp Ala Phe Thr Gly Ile Ala Lys Gly Asn
            100                 105                 110

Leu Asp His Met Pro Thr Lys Ala Glu Phe Asn Ala Cys Cys Arg Leu
        115                 120                 125

Tyr Arg Asp Gly Ala Gly Asn Tyr Tyr Pro Pro Leu Ala Phe Asp
    130                 135                 140

Lys Ile Ser Val Pro Ala Gln Leu Glu Glu Thr Trp Gly Met Met Glu
145                 150                 155                 160

Ala Lys Glu Arg Asn Lys Leu Arg Phe Gln Tyr Lys Leu Asp Val Trp
                165                 170                 175

Asn His Ala His Ala Asp Met Gly Ile Thr Gly Thr Glu Ile Phe Tyr
            180                 185                 190

Gln Thr Asp Lys Asn Ile Lys Leu Asp Arg Asn Tyr Lys Leu Arg Pro
        195                 200                 205

Glu Asp Arg Tyr Val Gln Thr Glu Arg Tyr Gly Arg Arg Glu Ile Gln
    210                 215                 220

Lys Arg Tyr Gln His Glu Leu Gln Ala Gly Ser Leu Leu Pro Asp Ile
225                 230                 235                 240

Met Ile Lys Thr Pro Lys Asn Asp Ile His Phe Val Tyr Arg Phe Ala
                245                 250                 255

Gly Asp Asn Tyr Ala Asn Lys Gln Phe Ser Glu Phe Glu His Thr Val
            260                 265                 270

Lys Arg Arg Tyr Gly Gly Glu Thr Glu Ile Lys Leu Lys Ser Lys Ser
        275                 280                 285

Gly Ile Met His Asp Ser Lys Tyr Leu Glu Ser Trp Glu Arg Gly Ser
    290                 295                 300

Ala Asp Ile Arg Phe Ala Glu Phe Val Gly Glu Asn Arg Ala His Asn
305                 310                 315                 320

Arg Gln Phe Pro Thr Ala Thr Val Asn Met Gly Gln Gln Pro Asp Gly
                325                 330                 335

```
Gln Gly Gly Leu Thr Arg Asp Arg His Val Ser Val Glu Phe Leu Met
            340                 345                 350

Gln Ser Ala Pro Asn Ser Pro Trp Ala Gln Ala Leu Lys Lys Gly Glu
            355                 360                 365

Leu Trp Asp Arg Val Gln Leu Leu Ala Arg Asp Gly Asn Arg Tyr Leu
            370                 375                 380

Ser Pro His Arg Leu Glu Tyr Ser Asp Pro Glu His Phe Thr Glu Leu
385                 390                 395                 400

Met Asn Arg Val Gly Leu Pro Ala Ser Met Gly Arg Gln Ser His Ala
                405                 410                 415

Ala Ser Ile Lys Phe Glu Lys Phe Asp Ala Gln Ala Val Ile Val
                420                 425                 430

Ile Asn Gly Pro Glu Leu Arg Asp Ile His Asp Leu Ser Pro Glu Asn
                435                 440                 445

Leu Gln Asn Val Ser Thr Lys Asp Val Ile Val Ala Asp Arg Asn Glu
            450                 455                 460

Asn Gly Gln Arg Thr Gly Thr Tyr Thr Ser Val Ala Glu Tyr Glu Arg
465                 470                 475                 480

Leu Gln Leu Arg Leu Pro Ala Asp Ala Ala Gly Val Leu Gly Glu Ala
                485                 490                 495

Ala Asp Lys Tyr Ser Arg Asp Phe Val Arg Pro Glu Pro Ala Ser Arg
            500                 505                 510

Pro Ile Ser Asp Ser Arg Arg Ile Tyr Glu Ser Arg Pro Arg Ser Gln
            515                 520                 525

Ser Val Asn Ser Phe
            530

<210> SEQ ID NO 22
<211> LENGTH: 672
<212> TYPE: PRT
<213> ORGANISM: Artificial Sequence
<220> FEATURE:
<223> OTHER INFORMATION: Description of Artificial Sequence: sequence of
      virE3_pTi15955 (1-2019)
<220> FEATURE:
<221> NAME/KEY: SITE
<222> LOCATION: (1)..(627)

<400> SEQUENCE: 22

Met Val Ser Thr Thr Lys Lys Ser Phe Ala Lys Ser Leu Thr Ala Asp
  1               5                  10                  15

Met Arg Arg Ser Ala Gln Arg Val Val Glu Gln Met Arg Lys Ala Leu
                20                  25                  30

Ile Thr Glu Glu Glu Ala Leu Lys Arg Gln Thr Arg Leu Glu Ser Pro
            35                  40                  45

Asp Arg Lys Arg Lys Tyr Ala Ala Asp Met Ala Ile Val Asp Lys Leu
        50                  55                  60

Asp Val Gly Phe Arg Gly Glu Ile Gly Tyr Lys Ile Leu Gly Asn Lys
 65                  70                  75                  80

Arg Leu Arg Val Asp Asn Pro Lys Glu Leu Thr Arg Glu His Gly Arg
                85                  90                  95

Leu Arg Lys Thr Lys Thr Val Leu Lys Arg Asn Pro Val Thr Gln Glu
            100                 105                 110

Val Tyr Leu Gly Leu His Glu Arg Lys Ser Trp Leu Ser Val Ser Ser
            115                 120                 125

His Leu Tyr Ala Ala Asp Gly Thr Leu Arg Met Lys His Val Lys Tyr
```

```
                130             135             140
Lys Asp Gly Arg Phe Glu Glu Arg Trp Glu Arg Asp Glu Asn Gly Asp
145                 150                 155                 160

Leu Ile Arg Thr Arg Tyr Ala Asn Arg Gly Arg Leu Phe Gln Pro Val
                165                 170                 175

Ser Glu Lys Met Gly Ala Pro Tyr Arg Ser Gly Pro Asp Asn Arg Leu
            180                 185                 190

Tyr Arg Asp Leu Thr Arg Gln Asn Gly Phe Arg Arg Glu Thr Phe Glu
            195                 200                 205

Arg Asp Asp Gln Gly Asn Leu Glu Arg Ile Gly Ser Asn His Val Gly
        210                 215                 220

Phe Ser Lys Ile Ser Val Lys Ala Ala Asn Arg Gln Thr Ser Gln Thr
225                 230                 235                 240

Lys Ile Gln Lys Leu Gly Gly Ala Phe Asn Lys Ser Phe Arg Ser Leu
                245                 250                 255

Leu Asp Lys Glu Gly Asn Glu Leu Gly Arg Asp Ile Leu Ser His Arg
            260                 265                 270

Arg Leu Tyr Asn Lys Arg Ser Ala Val Tyr Asp Glu Ala Thr Gly Gln
        275                 280                 285

Leu Lys Ser Ala Lys His Thr Phe Gly Lys Ile Tyr Arg Ser Glu Thr
    290                 295                 300

Asp Tyr Leu Ser Ala Gly Leu Lys Lys Val Ser Lys Lys Ile Leu Gly
305                 310                 315                 320

Val Thr Val Tyr Arg Lys Phe Ala Ala Leu Ser Glu Arg Glu Ser Glu
                325                 330                 335

Ala Glu Arg Leu Arg Ser Phe Glu Ser Gly Ala His Arg Gln Ile Trp
            340                 345                 350

Gln Glu Arg Ala Ala Thr Pro Gly Ser Pro Ser Glu Ser Asp Asp
        355                 360                 365

Ile His Phe Ala Gln Gln Ser His Leu Ala Lys Ala Asn Ser Asp His
        370                 375                 380

Val Glu Ala Asp Val Met Arg Val Thr Asp Gln His Ile Asp Val Ala
385                 390                 395                 400

Gly Gln Thr Ser Ser Ser Arg Gln Arg Asn Leu Glu Glu Arg Leu Asp
                405                 410                 415

Ser Gln Ser Arg Tyr Lys Pro Ala Asn Met Leu Leu Ser Asp Pro Asp
            420                 425                 430

Leu Arg Ala Asp Gly Pro Arg Pro Tyr Glu Gly Leu Ala Glu Leu Thr
        435                 440                 445

Leu Arg Arg Asp Asn Glu Ser Asp Gly His Lys Glu Asn Asp Gln Arg
    450                 455                 460

Leu Arg His Phe Leu Gln Pro Glu Pro Leu Val Leu Pro His Pro Gly
465                 470                 475                 480

Ser Pro Glu Ile Thr Lys Val Phe Gly Ser Arg Gly Glu Pro Leu His
                485                 490                 495

Pro Ser Gly Thr Leu His Thr Ala Val Gly Glu Thr Ala Cys Glu Ala
            500                 505                 510

Pro Val Met Ser Ser Ser Leu Asp Asn His Gln Pro Ala Pro Gly Gln
        515                 520                 525

Gln Glu Leu Leu Ser Leu Leu His Asn Ala Pro Ala Pro Val Ser Val
    530                 535                 540

Ala Ile His Asp Glu Gln Glu Arg Leu Ala Gly Glu Ala Pro Gly Gly
545                 550                 555                 560
```

```
Ser Phe Arg Gly Ser Ser Gly Arg Thr Ser Ser Met Ser Glu Ser Ile
                565                 570                 575

Phe Asp Glu Asp Val Gln Ser His Leu Val Arg Asp Tyr Ser Ile Asn
            580                 585                 590

Pro Thr Asn Gly Phe Ile Asp Pro Gln Ser Leu Phe Gly Gly Pro Asp
        595                 600                 605

Leu Ser Arg Gly Pro Lys Ser Gly Pro Glu Ile Pro Ser Glu Asp Tyr
    610                 615                 620

His Leu Ser Ala Ser Glu Gln Glu Asn Leu Leu Asn Gln Leu Leu Ser
625                 630                 635                 640

Val Pro Leu Pro Ile Pro Ser Pro Lys Pro Lys Ser Ala Arg Ser Met
                645                 650                 655

Ile Phe Glu Gly Ser Arg Pro Arg Glu Arg Ser Thr Ser Arg Gly Phe
            660                 665                 670
```

<210> SEQ ID NO 23
<211> LENGTH: 709
<212> TYPE: PRT
<213> ORGANISM: Artificial Sequence
<220> FEATURE:
<223> OTHER INFORMATION: Description of Artificial Sequence: derived
      amino acid sequence of RSF1010_mobA (1-2130)
<220> FEATURE:
<221> NAME/KEY: SITE
<222> LOCATION: (1)..(709)

<400> SEQUENCE: 23

```
Met Ala Ile Tyr His Leu Thr Ala Lys Thr Gly Ser Arg Ser Gly Gly
  1               5                  10                  15

Gln Ser Ala Arg Ala Lys Ala Asp Tyr Ile Gln Arg Glu Gly Lys Tyr
             20                  25                  30

Ala Arg Asp Met Asp Glu Val Leu His Ala Glu Ser Gly His Met Pro
         35                  40                  45

Glu Phe Val Glu Arg Pro Ala Asp Tyr Trp Asp Ala Ala Asp Leu Tyr
     50                  55                  60

Glu Arg Ala Asn Gly Arg Leu Phe Lys Glu Val Glu Phe Ala Leu Pro
 65                  70                  75                  80

Val Glu Leu Thr Leu Asp Gln Gln Lys Ala Leu Ala Ser Glu Phe Ala
                 85                  90                  95

Gln His Leu Thr Gly Ala Glu Arg Leu Pro Tyr Thr Leu Ala Ile His
            100                 105                 110

Ala Gly Gly Gly Glu Asn Pro His Cys His Leu Met Ile Ser Glu Arg
        115                 120                 125

Ile Asn Asp Gly Ile Glu Arg Pro Ala Ala Gln Trp Phe Lys Arg Tyr
    130                 135                 140

Asn Gly Lys Thr Pro Glu Lys Gly Gly Ala Gln Lys Thr Glu Ala Leu
145                 150                 155                 160

Lys Pro Lys Ala Trp Leu Glu Gln Thr Arg Glu Ala Trp Ala Asp His
                165                 170                 175

Ala Asn Arg Ala Leu Glu Arg Ala Gly His Asp Ala Arg Ile Asp His
            180                 185                 190

Arg Thr Leu Glu Ala Gln Gly Ile Glu Arg Leu Pro Gly Val His Leu
        195                 200                 205

Gly Pro Asn Val Val Glu Met Glu Gly Arg Gly Ile Arg Thr Asp Arg
    210                 215                 220

Ala Asp Val Ala Leu Asn Ile Asp Thr Ala Asn Ala Gln Ile Ile Asp
```

-continued

```
            225                 230                 235                 240
Leu Gln Glu Tyr Arg Glu Ala Ile Asp His Glu Arg Asn Arg Gln Ser
                245                 250                 255
Glu Glu Ile Gln Arg His Gln Arg Val Ser Gly Ala Asp Arg Thr Ala
            260                 265                 270
Gly Pro Glu His Gly Asp Thr Gly Arg Arg Ser Pro Ala Gly His Glu
            275                 280                 285
Pro Asp Pro Ala Gly Gln Arg Gly Ala Gly Gly Val Ala Glu Ser
        290                 295                 300
Pro Ala Pro Asp Arg Gly Gly Met Gly Gly Ala Gly Gln Arg Val Ala
305                 310                 315                 320
Gly Gly Ser Arg Arg Gly Glu Gln Arg Arg Ala Glu Arg Pro Glu Arg
                325                 330                 335
Val Ala Gly Val Ala Leu Glu Ala Met Ala Asn Arg Asp Ala Gly Phe
            340                 345                 350
His Asp Ala Tyr Gly Gly Ala Ala Asp Arg Ile Val Ala Leu Ala Arg
            355                 360                 365
Pro Asp Ala Thr Asp Asn Arg Gly Arg Leu Asp Leu Ala Ala Leu Gly
            370                 375                 380
Gly Pro Met Lys Asn Asp Arg Thr Leu Gln Ala Ile Gly Arg Gln Leu
385                 390                 395                 400
Lys Ala Met Gly Cys Glu Arg Phe Asp Ile Gly Val Arg Asp Ala Thr
                405                 410                 415
Thr Gly Gln Met Met Asn Arg Glu Trp Ser Ala Ala Glu Val Leu Gln
            420                 425                 430
Asn Thr Pro Trp Leu Lys Arg Met Asn Ala Gln Gly Asn Asp Val Tyr
            435                 440                 445
Ile Arg Pro Ala Glu Gln Arg His Gly Leu Val Leu Val Asp Asp
            450                 455                 460
Leu Ser Glu Phe Asp Leu Asp Asp Met Lys Ala Glu Gly Arg Glu Pro
465                 470                 475                 480
Ala Leu Val Val Glu Thr Ser Pro Lys Asn Tyr Gln Ala Trp Val Lys
                485                 490                 495
Val Ala Asp Ala Ala Gly Gly Glu Leu Arg Gly Gln Ile Ala Arg Thr
            500                 505                 510
Leu Ala Ser Glu Tyr Asp Ala Asp Pro Ala Ser Ala Asp Ser Arg His
            515                 520                 525
Tyr Gly Arg Leu Ala Gly Phe Thr Asn Arg Lys Asp Lys His Thr Thr
            530                 535                 540
Arg Ala Gly Tyr Gln Pro Trp Val Leu Leu Arg Glu Ser Lys Gly Lys
545                 550                 555                 560
Thr Ala Thr Ala Gly Pro Ala Leu Val Gln Gln Ala Gly Gln Gln Ile
                565                 570                 575
Glu Gln Ala Gln Arg Gln Glu Lys Ala Arg Arg Leu Ala Ser Leu
            580                 585                 590
Glu Leu Pro Glu Arg Gln Leu Ser Arg His Arg Thr Ala Leu Asp
            595                 600                 605
Glu Tyr Arg Ser Glu Met Ala Gly Leu Val Lys Arg Phe Gly Asp Asp
            610                 615                 620
Leu Ser Lys Cys Asp Phe Ile Ala Ala Gln Lys Leu Ala Ser Arg Gly
625                 630                 635                 640
Arg Ser Ala Glu Glu Ile Gly Lys Ala Met Ala Glu Ala Ser Pro Ala
                645                 650                 655
```

```
Leu Ala Glu Arg Lys Pro Gly His Glu Ala Asp Tyr Ile Glu Arg Thr
            660                 665                 670

Val Ser Lys Val Met Gly Leu Pro Ser Val Gln Leu Ala Arg Ala Glu
        675                 680                 685

Leu Ala Arg Ala Pro Ala Pro Arg Gln Arg Gly Met Asp Arg Gly Gly
690                 695                 700

Pro Asp Phe Ser Met
705

<210> SEQ ID NO 24
<211> LENGTH: 833
<212> TYPE: PRT
<213> ORGANISM: Artificial Sequence
<220> FEATURE:
<223> OTHER INFORMATION: Description of Artificial Sequence: translation
      of VirD5 pTi15955 (1-2502)
<220> FEATURE:
<221> NAME/KEY: SITE
<222> LOCATION: (1)..(833)

<400> SEQUENCE: 24

Met Thr Gly Lys Ser Lys Val His Ile Arg Ser Ser Ala Asp Thr Leu
1               5                   10                  15

Pro Asp Gly Ser Ile Thr Ala Pro Phe Ser Thr Gly Leu Ser Gly Asp
            20                  25                  30

Gln Ala Asp Ala Ser Phe Glu Ala Gln Thr Asp Tyr Ser Gln Ser Thr
        35                  40                  45

Ser Val Ser Phe Thr Tyr Asp Gly Val Lys Leu Gly Pro Ala Glu Arg
    50                  55                  60

Ala Ala Tyr Glu Asn Trp Cys Glu Pro Gly Arg Pro Thr Trp Lys Asp
65                  70                  75                  80

Leu Ile Ile Lys Ala Arg Val Asp Pro Ile Asp Val Ile Trp Leu
                85                  90                  95

Arg Asp Leu Glu Glu Asp Thr Pro Ser Thr Phe Arg Tyr Glu Gly Met
            100                 105                 110

Pro Leu Gly Leu Gly Glu Arg Lys Ala Tyr Glu Asn Trp Gln Glu Asp
        115                 120                 125

Ala Gln Pro Thr Trp Glu Asp Leu Val Val Ser Ala Arg Met Thr Glu
    130                 135                 140

Leu Gly Arg Pro His Gly Ile Thr Gly Glu Tyr Thr Ser Leu Ala Gly
145                 150                 155                 160

Ser Lys Asn Thr Ser Ser Ile Ser Leu Lys Arg Lys Arg Ser Asn Leu
                165                 170                 175

Ile Asp Asp Glu Asn Ser Ser Gly Ser Phe Ser Tyr Asp Gly Met Lys
            180                 185                 190

Leu Gly Glu Ala Glu Arg Ser Ala Tyr Gly Asp Trp Ala Glu Ala Glu
        195                 200                 205

Pro Pro Thr Trp Lys Asp Leu Val Leu Arg Ala Arg Val Ser Ser Ile
    210                 215                 220

Asn Asp Ser Ala Trp Leu Phe Asp Ser Gln Thr Ser Ser Ser Ser Phe
225                 230                 235                 240

Glu Tyr Asn Gly Val Pro Leu Gly Glu Pro Glu Arg Gln Ala Leu Arg
                245                 250                 255

Gln Trp Gln Gly Asp Ala Gln Pro Thr Trp Glu Asp Leu Val Val Asn
            260                 265                 270

Ala Arg Met Ala Glu Leu Cys His Ala Gly Trp Ile Glu Gly Gln Lys
```

-continued

```
              275                 280                 285
Gly Cys Phe Glu Lys Arg Gly Glu Ala Leu His Ala Ser Glu Arg Gly
            290                 295                 300

Ser Gln Arg Pro Ile Val Gln Arg Thr Asp Ser Ser Asp Ser Phe Leu
305                 310                 315                 320

Tyr Asp Gly Arg Arg Leu Gly Ala Pro Glu Arg Thr Ala Tyr Glu Arg
                325                 330                 335

Trp Ser Lys Arg Glu Arg Pro Thr Trp Glu Asp Leu Ile Leu Asp Ala
            340                 345                 350

His Gln Ala Arg Ile Glu Ser Asp Ala Val Thr Thr Gln Ala Ile Gly
        355                 360                 365

Gln Ser Ser Ser Leu Val Phe Leu Tyr Glu Gly Lys Ser Leu Gly Cys
    370                 375                 380

Arg Glu Arg Glu Ala Tyr Glu Lys Trp Arg Gln Pro Ala Gln Pro Arg
385                 390                 395                 400

Trp Gln Asn Leu Val Val Asn Ala Arg Leu Ala Glu Leu Asp Pro Ser
                405                 410                 415

Val Trp Ile Ala Asp Glu Arg Asp Pro Leu Asp Asp Gly Asp Ala Leu
            420                 425                 430

Gly Arg Pro Ser Tyr Thr Ser Leu Thr Asp Arg Ser Asp Val Pro Leu
        435                 440                 445

Asp Asp Gln Ser Ile Tyr His Arg Ser Asp Leu Val Arg Glu Gln Val
    450                 455                 460

Ser Glu Ser Ser Gln Lys Gln Phe Ala Ala Cys Ser Glu Ser Glu Thr
465                 470                 475                 480

Ile Pro Val Ser Trp Phe Thr Ala Ser Gly Leu Asp Ala Asn Asn Thr
                485                 490                 495

Glu Asn Ile Ala Ala Ser Asp Pro Val Asp Gly Thr Gly Val Lys
            500                 505                 510

Arg Leu Gly Ser Lys Ser Asp Arg Thr Val Thr Ala Ser Ile His Asp
        515                 520                 525

Val Asn Ser Ser Thr Lys Arg Leu Leu Leu Asn Glu Phe Gly Leu Glu
    530                 535                 540

Ala Pro Arg Pro Ser Pro Glu Lys Thr Val Arg Leu Arg Ser Asp Asn
545                 550                 555                 560

Ile Gly Thr Tyr Gly Ser Arg Arg Asn Glu Arg Met Arg Leu Ala Thr
                565                 570                 575

Glu Thr Gly Ala Tyr Glu Ser Glu His Ile Phe Gly Phe Lys Ala Val
            580                 585                 590

His Asp Thr Ala Arg Ala Thr Lys Glu Gly Arg Arg Leu Glu Arg Pro
        595                 600                 605

Met Pro Ala Tyr Leu Glu Tyr Lys Gly Leu His Arg Gln His Val Gly
    610                 615                 620

Thr Gly Arg Gly Arg Thr Lys Leu Val Gly Arg Gly Trp Pro Asp Asp
625                 630                 635                 640

Thr Ser Tyr Arg Ser Asp Gln Arg Ala Thr Leu Ser Asp Pro Val Ala
                645                 650                 655

Arg Ser Glu Gly Ala Thr Ala Ser Asn Gly Tyr Gln Leu Asn Gln Leu
            660                 665                 670

Gly Tyr Ala His Gln Leu Ala Ser Asp Gly Leu Gln Ser Glu Ser Pro
        675                 680                 685

Asp Gly Val Ala Leu Pro Ile Gln Val Ala Thr Thr Ser Tyr Asn Tyr
    690                 695                 700
```

-continued

```
Thr Val Ser Arg Asp Pro Val Leu Val Pro Pro Asp Lys Asn Glu Ala
705                 710                 715                 720

Pro Gln Leu Leu His Leu Gly Pro Arg Gly Gln Thr Glu Ala Val Leu
                725                 730                 735

Ala Arg Glu Thr Ala Leu Thr Gly Lys Trp Pro Thr Leu Glu Arg Glu
            740                 745                 750

Gln Gln Val Tyr Arg Glu Phe Leu Ala Leu Tyr Asp Val Lys Lys Asp
                755                 760                 765

Leu Glu Ala Lys Ser Val Gly Val Arg Gln Lys Lys Glu Val Ser
770                 775                 780

Ser Ala Leu Asp Arg Thr Ala Arg Leu Ile Ile Thr Ser Pro Ser Lys
785                 790                 795                 800

Ala Arg Ser Glu Ala Glu Thr Glu Lys Ala Ile Asp Glu Leu Asp Asp
                805                 810                 815

Arg Arg Val Tyr Asp Pro Arg Asp Arg Ala Gln Asp Lys Ala Phe Lys
                820                 825                 830

Arg
```

```
<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: alignment
      of the C-terminal of virF
<220> FEATURE:
<221> NAME/KEY: SITE
<222> LOCATION: (1)..(36)

<400> SEQUENCE: 25
```

```
Glu Val Met Ala Glu Val Arg Pro Ile Ala Arg Ser Ile Lys Thr Ala
 1               5                  10                  15

His Asp Asp Ala Arg Ala Glu Leu Met Ser Ala Asp Arg Pro Arg Ser
                20                  25                  30

Thr Arg Gly Leu
            35
```

```
<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: alignment
      of the C-terminal of virE2
<220> FEATURE:
<221> NAME/KEY: SITE
<222> LOCATION: (1)..(38)

<400> SEQUENCE: 26
```

```
Ala Ala Asp Lys Tyr Ser Arg Asp Phe Val Arg Pro Glu Pro Ala Ser
 1               5                  10                  15

Arg Pro Ile Ser Asp Ser Arg Arg Ile Tyr Glu Ser Arg Pro Arg Ser
                20                  25                  30

Gln Ser Val Asn Ser Phe
            35
```

```
<210> SEQ ID NO 27
<211> LENGTH: 39
<212> TYPE: PRT
<213> ORGANISM: Artificial Sequence
<220> FEATURE:
```

```
<223> OTHER INFORMATION: Description of Artificial Sequence: alignment
      of the C-terminal of virE3
<220> FEATURE:
<221> NAME/KEY: SITE
<222> LOCATION: (1)..(39)

<400> SEQUENCE: 27

Leu Leu Asn Gln Leu Leu Ser Val Pro Leu Pro Ile Pro Ser Pro Lys
 1               5                  10                  15

Pro Lys Ser Ala Arg Ser Met Ile Phe Glu Gly Ser Arg Pro Arg Glu
                20                  25                  30

Arg Ser Thr Ser Arg Gly Phe
                35

<210> SEQ ID NO 28
<211> LENGTH: 42
<212> TYPE: PRT
<213> ORGANISM: Artificial Sequence
<220> FEATURE:
<223> OTHER INFORMATION: Description of Artificial Sequence: alignment
      of the C-terminal of VirD2
<220> FEATURE:
<221> NAME/KEY: SITE
<222> LOCATION: (1)..(42)

<400> SEQUENCE: 28

Ser Ala Ser Ile Gly Thr Glu Gln Pro Glu Ala Ser Pro Lys Arg Pro
 1               5                  10                  15

Arg Asp Arg His Asp Gly Glu Leu Gly Gly Arg Lys Arg Ala Arg Gly
                20                  25                  30

Asn Arg Arg Asp Asp Gly Arg Gly Gly Thr
                35                  40

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: alignment
      of the C-terminal of VirD5
<220> FEATURE:
<221> NAME/KEY: SITE
<222> LOCATION: (1)..(39)

<400> SEQUENCE: 29

Ile Thr Ser Pro Ser Lys Ala Arg Ser Glu Ala Glu Thr Glu Lys Ala
 1               5                  10                  15

Ile Asp Glu Leu Asp Asp Arg Arg Val Tyr Asp Pro Arg Asp Arg Ala
                20                  25                  30

Gln Asp Lys Ala Phe Lys Arg
                35

<210> SEQ ID NO 30
<211> LENGTH: 42
<212> TYPE: PRT
<213> ORGANISM: Artificial Sequence
<220> FEATURE:
<223> OTHER INFORMATION: Description of Artificial Sequence: alignment
      of the C-terminal of mobA
<220> FEATURE:
<221> NAME/KEY: SITE
<222> LOCATION: (1)..(42)

<400> SEQUENCE: 30

Tyr Ile Glu Arg Thr Val Ser Lys Val Met Gly Leu Pro Ser Val Gln
 1               5                  10                  15
```

```
-continued

Leu Ala Arg Ala Glu Leu Ala Arg Ala Pro Ala Pro Arg Gln Arg Gly
             20                  25                  30

Met Asp Arg Gly Gly Pro Asp Phe Ser Met
             35                  40
```